(12) United States Patent
Reshatoff et al.

(10) Patent No.: US 8,703,421 B2
(45) Date of Patent: Apr. 22, 2014

(54) COMPOSITIONS, KITS AND RELATED METHODS FOR THE DETECTION AND/OR MONITORING OF SALMONELLA

(75) Inventors: Michael R. Reshatoff, San Diego, CA (US); Edgar O. Ong, San Diego, CA (US); James J. Hogan, Coronado, CA (US)

(73) Assignee: Gen-Probe Incorporated, San Diego, CA (US)

( * ) Notice: Subject to any disclaimer, the term of this patent is extended or adjusted under 35 U.S.C. 154(b) by 500 days.

(21) Appl. No.: 12/995,168

(22) PCT Filed: May 29, 2009

(86) PCT No.: PCT/US2009/045738
§ 371 (c)(1),
(2), (4) Date: Nov. 29, 2010

(87) PCT Pub. No.: WO2009/158119
PCT Pub. Date: Dec. 30, 2009

(65) Prior Publication Data
US 2011/0117564 A1    May 19, 2011

Related U.S. Application Data

(60) Provisional application No. 61/057,787, filed on May 30, 2008.

(51) Int. Cl.
*C12Q 1/68* (2006.01)
*C12P 19/34* (2006.01)
*C07H 21/04* (2006.01)

(52) U.S. Cl.
USPC ............. 435/6.12; 435/91.2; 536/24.33

(58) Field of Classification Search
USPC .................. 435/6.12, 91.2; 536/24.33
See application file for complete search history.

(56) References Cited

U.S. PATENT DOCUMENTS

| | | | |
|---|---|---|---|
| 4,486,539 A | 12/1984 | Ranki et al. | |
| 4,581,333 A | 4/1986 | Kourilsky et al. | |
| 4,683,195 A | 7/1987 | Mullis et al. | |
| 4,683,202 A | 7/1987 | Mullis | |
| 4,751,177 A | 6/1988 | Stabinsky | |
| 4,800,159 A | 1/1989 | Mullis et al. | |
| 4,894,324 A | 1/1990 | Himmelmann et al. | |
| 4,965,188 A | 10/1990 | Mullis et al. | |
| 5,030,557 A | 7/1991 | Hogan et al. | |
| 5,118,801 A | 6/1992 | Lizardi et al. | |
| 5,130,238 A | 7/1992 | Malek et al. | |
| 5,185,439 A | 2/1993 | Arnold et al. | |
| 5,270,184 A | 12/1993 | Walker et al. | |
| 5,288,609 A | 2/1994 | Engelhardt et al. | |
| 5,312,728 A | 5/1994 | Lizardi et al. | |
| 5,399,491 A | 3/1995 | Kacian et al. | |
| 5,455,166 A | 10/1995 | Walker | |
| 5,480,784 A | 1/1996 | Kacian et al. | |
| 5,539,082 A | 7/1996 | Nielsen et al. | |
| 5,547,842 A | 8/1996 | Hogan et al. | |
| 5,585,481 A | 12/1996 | Arnold et al. | |
| 5,639,599 A | 6/1997 | Ryder et al. | |
| 5,639,604 A | 6/1997 | Arnold et al. | |
| 5,656,207 A | 8/1997 | Woodhead et al. | |
| 5,658,737 A | 8/1997 | Nelson et al. | |
| 5,731,148 A | 3/1998 | Becker et al. | |
| 5,925,517 A | 7/1999 | Tyagi et al. | |
| 5,948,899 A | 9/1999 | Arnold et al. | |
| 6,004,745 A | 12/1999 | Arnold et al. | |
| 6,031,091 A | 2/2000 | Arnold et al. | |
| 6,060,237 A | 5/2000 | Nygren et al. | |
| 6,110,678 A | 8/2000 | Weisburg et al. | |
| 6,130,038 A | 10/2000 | Becker et al. | |
| 6,150,517 A * | 11/2000 | Hogan et al. ............... 536/25.3 |
| 6,268,490 B1 | 7/2001 | Imanishi et al. | |
| 6,361,945 B1 | 3/2002 | Becker et al. | |
| 6,414,152 B1 | 7/2002 | Campbell et al. | |
| 6,534,273 B2 | 3/2003 | Weisburg et al. | |
| 6,670,461 B1 | 12/2003 | Wengel et al. | |
| 6,835,542 B2 | 12/2004 | Becker et al. | |
| 6,849,412 B2 | 2/2005 | Becker et al. | |
| 7,374,885 B2 | 5/2008 | Becker et al. | |
| 2003/0022177 A1 * | 1/2003 | Wittwer et al. ............. 435/6 |
| 2005/0287591 A1 * | 12/2005 | Browne ........................ 435/6 |
| 2006/0068417 A1 | 3/2006 | Becker et al. | |
| 2006/0276972 A1 | 12/2006 | Light, II et al. | |

FOREIGN PATENT DOCUMENTS

| | | |
|---|---|---|
| DE | 19915141 | 9/2000 |
| EP | 0 370 694 | 5/1990 |
| EP | 0 684 315 | 6/2002 |
| WO | WO-00/58505 | 10/2000 |
| WO | WO-02/14555 | 2/2002 |
| WO | WO-03/095677 | 11/2003 |
| WO | WO-2006/026388 | 3/2006 |

OTHER PUBLICATIONS

Lowe et al. (Nucleic acid research, 1990,vol. 18(7), p. 1757-1761.*
The nucleic acid sequence search reports: AC: AAF23096 & AEE92232 searched Mar. 15, 2013.*
Communication pursuant to Article 94(3) EPC, European Application No. 09 770 654.3, dated Jun. 5, 2013.
Carruthers, et al, Chemical synthesis of deoxyoligonucleotides by the phosphoramidite method, Methods Enzymol, 154:287-313 (1987).
Glen Research Corporation, Products for DNA Research, Catalog No. 10-1909-xx, Spacer Phosphoramidite 9; May 3, 2010.
Glen Research Corporation, Products for DNA Research, Catalog No. 20-0102-01; dC=5'-CPG; May 3, 2010.
Guatelli, et al, Isothermal, in vitro amplification of nucleic acids by a multienzyme reaction modeled after retroviral replication, Proc. Natl. Acad. Sci., 87(5):1874-1878 (1990).

(Continued)

*Primary Examiner* — Kenneth R. Horlick
*Assistant Examiner* — Joyce Tung
(74) *Attorney, Agent, or Firm* — Jeffrey E. Landes

(57) ABSTRACT

Provided are compositions, kits, and methods for the identification of *Salmonella*. In certain aspects and embodiments, the compositions, kits, and methods may provide improvements in relation to specificity, sensitivity, and speed of detection.

15 Claims, 2 Drawing Sheets

(56) References Cited

OTHER PUBLICATIONS

International Search Report dated Mar. 5, 2010 in application PCT/US2009/045738.

Kwoh, et al, Transcription-based amplification system and detection of amplified human immunodeficiency virus type 1 with a bead-based sandwich hybridization format, Proc. Natl. Acad. Sci., 86:1173-1177 (1989).

Lizardi, et al, Exponential Amplification of Recombinant-RNA Hybridization Probes, Nature Biotechnology, 6:1197-1202 (1988).

Majlessi, et al, Advantages of 2'-O-methyl oligoribonucleotide probes for detecting RNA targets, Nucleic Acids Res., 26:2224-2229 (1998).

Petersen, et al, The conformations of locked nucleic acids (LNA), J. Mol. Recognit., 13:44-53 (2000).

Sambrook, et al, Molecular Cloning: A Laboratory Manual, (1989), Chapter 10.

Walker, et al, Isothermal in vitro amplification of DNA by a restriction enzyme/DNA polymerase system, Proc. Natl. Acad. Sci., (1992) 89:392-396.

Weiss, R., Hot prospect for new gene amplifier, Science, 254:1292-1293 (1991).

* cited by examiner

5'-TCACACTATCATTAACTGAATCCATAGGTTAATGAGGCGAACCGGGG
GAACTGAAACATCTAAGTACCCCGAGGAAAAGAAATCAACCGAGATTC
CCCCAGTAGCGGCGAGCGAACGGGGAGGAGCCCAGAGCCTGAATCAG
CATGTGTGTTAGTGGAAGCGTCTGGAAAGGCGCGCGATACAGGGTGAC
AGCCCCGTACACAAAAGCGCATGTGCTGTGAGCTCGATGAGTAGGGCG
GGACACGTGGTATCCTGTCTGAATATGG-3'

Fig. 2

COMPOSITIONS, KITS AND RELATED METHODS FOR THE DETECTION AND/OR MONITORING OF *SALMONELLA*

BACKGROUND OF THE INVENTION

The *Salmonella* genus is part of a large family of gram-negative bacteria found in humans, animals, foods and the environment. *Salmonella* is a rod-shaped enterobacteria that infects humans and causes typhoid fever, paratyphoid fever, and food-borne illness. In the U.S., it is the most frequently reported food-borne disease. Worldwide, it is the second most common food-borne illness in the world. Salmonellosis affects 100 to 300 per 100,000 population. In 2005, there were ~36,000 cases reported to the CDC. Salmonellosis is transmitted by the ingestion of food derived from infected animals or contaminated by feces (animal or human). Symptoms include acute enterocolitis with sudden onset of headache, abdominal pain, diarrhea, nausea and sometimes vomiting. Incubation time is between 6 to 72 h (average of 12-36 h). Enteric bacteria have complex genotypic and phenotypic characters that are oftentimes shared across genera. As a result, their genomes share many common sequences. There remains a need in the art for a rapid and robust detection system that can specifically and selectively identify *Salmonella* in a sample of interest.

SEQUENCE LISTING

The instant application contains a Sequence Listing which has been submitted in ASCII format via EFS-Web and is hereby incorporated by reference in its entirety. Said ASCII copy, created on Jun. 5, 2012, is named NEW-GP209-PCT-ST25-Correct5-2012.txt and is 43,873 bytes in size.

SUMMARY OF THE INVENTION

The present invention relates to compositions, kits, and methods used in the detection of *Salmonella*. The invention is based at least in part on the discovery that certain *Salmonella* sequences are surprisingly efficacious for the detection of *Salmonella*. In certain aspects and embodiments, particular regions of the *Salmonella* 23S rRNA have been identified as preferred targets for nucleic acid amplification reactions which provide improvements in relation to specificity, sensitivity, or speed of detection as well as other advantages.

Therefore, according to one aspect, there are provided compositions for use in a *Salmonella* nucleic acid amplification assay. In certain embodiments of the aspects provided herein, the compositions include a T7 provider oligonucleotide and a primer oligonucleotide; in which the T7 provider oligonucleotide targets a sequence in a region of *Salmonella* nucleic acid corresponding to bases from about 268-320 of *E. coli* 23S rRNA and the primer oligonucleotide targets a sequence in a region of *Salmonella* nucleic acid, in which the T7 and primer oligonucleotides used in the amplification assay target opposite strands of the *Salmonella* nucleic acid sequence to be amplified.

In a second aspect, there are provided compositions for use in a *Salmonella* nucleic acid amplification assay. In certain embodiments of the aspects provided herein, the compositions include a T7 provider oligonucleotide and a primer oligonucleotide; in which the T7 provider oligonucleotide targets a sequence in a region of *Salmonella* nucleic acid and the primer oligonucleotide targets a sequence in a region of *Salmonella* nucleic acid corresponding to bases from about 338-395 of *E. coli* 23S rRNA, in which the T7 and primer oligonucleotides used in the amplification assay target opposite strands of the *Salmonella* nucleic acid sequence to be amplified.

In a third aspect, there are provided kits that include the compositions provided herein. In certain embodiments of the aspects provided herein, the kits include a T7 provider oligonucleotide and a primer oligonucleotide, in which the T7 provider oligonucleotide targets a sequence in a region of *Salmonella* nucleic acid corresponding to bases from about 268-320 of *E. coli* 23S rRNA and the primer oligonucleotide targets a sequence in a region of *Salmonella* nucleic acid, in which the T7 and primer oligonucleotides used in the amplification assay target opposite strands of the *Salmonella* nucleic acid sequence to be amplified.

In a fourth aspect, there are provided kits that include the compositions provided herein. In certain embodiments of the aspects provided herein, the kits include a T7 provider oligonucleotide and a primer oligonucleotide, in which the T7 provider oligonucleotide targets a sequence in a region of *Salmonella* nucleic acid and the primer oligonucleotide targets a sequence in a region of *Salmonella* nucleic acid corresponding to bases from about 338-395 of *E. coli* 23S rRNA, in which the T7 and primer oligonucleotides used in the amplification assay target opposite strands of the *Salmonella* nucleic acid sequence to be amplified.

In a fifth aspect, there are provided methods for detecting the presence of *Salmonella* in a sample using the compositions and/or kits provided herein. In certain embodiments of the aspects provided herein, the methods use a T7 provider oligonucleotide and a primer oligonucleotide, in which the T7 provider oligonucleotide targets a sequence in a region of *Salmonella* nucleic acid corresponding to bases from about 268-320 of *E. coli* 23S rRNA and the primer oligonucleotide targets a sequence in a region of *Salmonella* nucleic acid, in which the T7 and primer oligonucleotides used in the amplification assay target opposite strands of the *Salmonella* nucleic acid sequence to be amplified.

In a sixth aspect, there are provided methods for detecting the presence of *Salmonella* in a sample using the compositions and/or kits provided herein. In certain embodiments of the aspects provided herein, the methods use a T7 provider oligonucleotide and a primer oligonucleotide, in which the T7 provider oligonucleotide targets a sequence in a region of *Salmonella* nucleic acid and the primer oligonucleotide targets a sequence in a region of *Salmonella* nucleic acid corresponding to bases from about 338-395 of *E. coli* 23S rRNA, in which the T7 and primer oligonucleotides used in the amplification assay target opposite strands of the *Salmonella* nucleic acid sequence to be amplified.

In one embodiment of the aspects provided herein, the T7 provider targets a sequence in a region of *Salmonella* nucleic acid corresponding to bases 268-302 of *E. coli* 23S rRNA. In another embodiment, the T7 provider targets a sequence in a region of *Salmonella* nucleic acid corresponding to bases 279-310 of *E. coli* 23S rRNA. In yet another embodiment, the T7 provider targets a sequence in a region of *Salmonella* nucleic acid corresponding to bases 279-309 of *E. coli* 23S rRNA. In a particular embodiment, the T7 provider targets a sequence in a region of *Salmonella* nucleic acid corresponding to bases 279-306 of *E. coli* 23S rRNA. In a certain embodiment, the T7 provider targets a sequence in a region of *Salmonella* nucleic acid corresponding to bases 279-302 of *E. coli* 23S rRNA.

In one embodiment of the aspects provided herein, the primer oligonucleotide targets a sequence in a region of *Salmonella* nucleic acid corresponding to bases 349-374 of *E. coli* 23S rRNA. In another embodiment, the primer oligonucleotide targets a sequence in a region of *Salmonella* nucleic acid corresponding to bases 349-370 of *E. coli* 23S rRNA. In yet another embodiment, the primer oligonucleotide targets a sequence in a region of *Salmonella* nucleic acid corresponding to bases 349-366 of *E. coli* 23S rRNA.

In certain embodiments of the aspects provided herein, the T7 provider is selected from the sequences of SEQ ID NOs: 1-34 and complements. In other embodiments, the primer oligonucleotide is selected from the sequences of SEQ ID NOs: 35-58 and complements, as defined herein. In some preferred embodiment, the T7 provider is selected from the sequences of SEQ ID NOs: 1-26 and complements. In other preferred embodiments, the primer oligonucleotide selected from the sequences of SEQ ID NOs: 35-51 and complements, as defined herein.

In one particularly preferred embodiment of the aspects provided herein, the T7 provider has the sequence of SEQ ID NO: 17 or complement. In another particularly preferred embodiment, the primer oligonucleotide has the sequence of SEQ ID NO: 50 or complement. In a particularly preferred embodiment, the T7 provider has the sequence of SEQ ID NO: 26 or complement. In another particularly preferred embodiment, the primer oligonucleotide has the sequence of SEQ ID NO: 49 or complement.

In certain embodiments of the compositions, methods and kits provided herein, the T7 provider oligonucleotide includes 15-35 nucleotides that are at least 70%; or 75%; or 80%; or 85%; or 90%; or 100% complementary to the targeted *Salmonella* nucleic acid sequence. In certain preferred embodiments, the T7 provider oligonucleotide includes 15-35 nucleotides that are complementary to the targeted *Salmonella* nucleic acid sequence but have 1 mismatch; or 2 mismatches; or 3 mismatches; or 5 mismatches as compared the targeted nucleic acid sequence within the 15-35 complimentary nucleotides.

In one embodiment of the aspects provided herein, the primer oligonucleotide includes 15-35 nucleotides that are at least 70%; or 75%; or 80%; or 85%; or 90% complementary to the targeted *Salmonella* nucleic acid sequence. In another embodiment, the primer oligonucleotide is 100% complementary to the targeted *Salmonella* nucleic acid sequence. In one preferred embodiment, the primer oligonucleotide includes 15-35 nucleotides that are complementary to the targeted *Salmonella* nucleic acid sequence but have 1 mismatch; or 2 mismatches; or 3 mismatches; or 5 mismatches as compared the targeted nucleic acid sequence within the 15-35 complimentary nucleotides.

In some embodiments of the aspects provided herein, one or more additional oligonucleotide types and/or other amplification reagents that serve to facilitate or improve one or more aspects of the transcription-mediated amplification reaction may be included. For example, in a preferred embodiment, in addition to a T7 provider and/or a primer oligonucleotide, additional oligonucleotides may further include one or more of a: detection oligonucleotide, blocker oligonucleotide, target capture oligonucleotide, and the like.

In one embodiment of the aspects provided herein, the compositions, kits, and/or methods may further include or use a detection oligonucleotide, preferably a torch oligonucleotide or molecular beacon. In a particular embodiment, the detection oligonucleotide is a torch oligonucleotide selected from the sequences of SEQ ID NOs: 66-70 and complements, as defined herein. In certain preferred embodiments, the detection oligonucleotide is a torch oligonucleotide selected from the sequences of SEQ ID NO: 66, SEQ ID NO: 67, and complements, as defined herein. In a particularly preferred embodiment, the detection oligonucleotide is a torch oligonucleotide having the sequence of SEQ ID NO: 66 or complement, as defined herein.

In one embodiment of the aspects provided herein, the compositions, kits, and/or methods may further include or use a blocker oligonucleotide. In a particular embodiment, the blocker oligonucleotide is selected from the sequences of SEQ ID NOs: 59-65 and complements, as defined herein. In certain preferred embodiments, the blocker oligonucleotide is selected from the sequences of SEQ ID NOs: 59, 61, 63, 64, and complements, as defined herein. In a particularly preferred embodiment, the blocker oligonucleotide has the sequence of SEQ ID NOs: 59 or complement, as defined herein.

In some embodiments of the aspects provided herein, the compositions, kits, and/or methods may further include or use a target capture oligonucleotide. In a particular embodiment, the target capture oligonucleotide is selected from the sequences of SEQ ID NOs: 71-77 and complements, as defined herein. In a preferred embodiment, the target capture oligonucleotide is selected from the sequences of SEQ ID NOs: 71, 74, and complements as defined herein. In a particularly preferred embodiment, the target capture oligonucleotide has the sequence of SEQ ID NOs: 74 or complement as defined herein.

In some aspects, there are provided compositions for use in a *Salmonella* transcription-mediated amplification assay (hereinafter "TMA"). In some aspects, there are provided kits for performing a *Salmonella* transcription-mediated amplification assay. In some aspects, there are provided methods for performing a *Salmonella* transcription-mediated amplification assay. In certain embodiments, the compositions, kits, and/or methods may include or use one or more oligonucleotides such as a: T7 provider, primer oligonucleotide, detection oligonucleotide, blocker oligonucleotide, Torch oligonucleotide, and the like.

The terms and concepts of the invention have meanings as set forth herein unless expressly stated to the contrary and/or unless context specifically dictates otherwise. Unless defined otherwise, scientific and technical terms used herein have the same meaning as commonly understood by those skilled in the relevant art. General definitions may be found in technical books relevant to the art of molecular biology, e.g., Dictionary of Microbiology and Molecular Biology, 2nd ed. (Singleton et al., 1994, John Wiley & Sons, New York, N.Y.) or The Harper Collins Dictionary of Biology (Hale & Marham, 1991, Harper Perennial, New York, N.Y.). Unless mentioned otherwise, techniques employed or contemplated herein are standard methodologies well known to one of ordinary skill in the art. The examples included herein illustrate some preferred embodiments. Each reference cited herein is specifically incorporated herein by reference in its entirety.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

The term "nucleic acid" as used herein encompasses a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, virus genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double-stranded or single-stranded form. Nucleic acids may include modified bases to alter the function or behavior of the nucleic acid, e.g., addition of a 3'-terminal dideoxynucleotide to block additional nucleotides from being added to the nucleic acid. As used herein, a "sequence" of a nucleic acid refers to the sequence of bases which make up a nucleic acid.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit which does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a "target sequence" to be amplified. Target nucleic acids may be DNA or RNA as described herein, and may be either single-stranded or double-stranded. The target nucleic acid may include other sequences besides the target sequence which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

By "isolated" it is meant that a sample containing a target nucleic acid is taken from its natural milieu, but the term does not connote any degree of purification.

The term "target sequence" as used herein refers to the particular nucleotide sequence of the target nucleic acid which is to be amplified. The "target sequence" includes the complexing sequences to which oligonucleotides (e.g., priming oligonucleotides and/or promoter oligonucleotides) complex during the processes of TMA. Where the target nucleic acid is originally single-stranded, the term "target sequence" will also refer to the sequence complementary to the "target sequence" as present in the target nucleic acid. Where the "target nucleic acid" is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

The term "targets a sequence" as used herein in reference to a region of *Salmonella* nucleic acid refers to a process whereby an oligonucleotide hybridizes to the target sequence in a manner that allows for amplification and detection as described herein. In one preferred embodiment, the oligonucleotide is complementary with the targeted *Salmonella* nucleic acid sequence and contains no mismatches. In another preferred embodiment, the oligonucleotide is complementary but contains 1; or 2; or 3; or 4; or 5 mismatches with the targeted *Salmonella* nucleic acid sequence. Preferably, the oligonucleotide that hybridizes to the *Salmonella* nucleic acid sequence includes at least 10 to 50; or 12 to 45; or 14 to 40; or 15-35 nucleotides complementary to the target sequence.

The term "fragment" or "region" as used herein in reference to the *Salmonella* targeted nucleic acid sequence refers to a piece of contiguous nucleic acid. In certain embodiments, the fragment includes 25; or 50; or 75; or 100; or 125; or 150; or 175; or 200; or 225; or 250; or 300; or 350; or 400; or 450; or 500; or 750; or 1000; or 2000; or 3000 nucleotides.

As used herein, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods disclosed herein, as well as subsequent detection methods. The oligonucleotide may be DNA and/or RNA and/or analogs thereof. The term oligonucleotide does not denote any particular function to the reagent, rather, it is used generically to cover all such reagents described herein. An oligonucleotide may serve various different functions, e.g., it may function as a primer if it is specific for and capable of hybridizing to a complementary strand and can further be extended in the presence of a nucleic acid polymerase, it may provide a promoter if it contains a sequence recognized by an RNA polymerase and allows for transcription (e.g., a T7 Provider), and it may function to prevent hybridization or impede primer extension if appropriately situated and/or modified.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

As used herein, an oligonucleotide "substantially corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from the referred to sequence and still hybridize to the same target nucleic acid sequence. This variation from the nucleic acid may be stated in terms of a percentage of identical bases within the sequence or the percentage of perfectly complementary bases between the probe or primer and its target sequence. Thus, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. One skilled in the art will understand the various modifications to the hybridization conditions that might be required at various percentages of complementarity to allow hybridization to a specific target sequence without causing an unacceptable level of non-specific hybridization.

A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557, the contents of which are incorporated by reference herein. Helpers may also be used to assist with the hybridization to target nucleic acid sequences and function of primer, target capture and other oligonucleotides.

As used herein, a "blocking moiety" is a substance used to "block" the 3'-terminus of an oligonucleotide or other nucleic acid so that it cannot be efficiently extended by a nucleic acid polymerase.

As used herein, a "priming oligonucleotide" or "primer" is an oligonucleotide, at least the 3'-end of which is complementary to a nucleic acid template, and which complexes (by hydrogen bonding or hybridization) with the template to give a primer: template complex suitable for initiation of synthesis by an RNA- or DNA-dependent DNA polymerase.

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter-provider" or "provider" refers to an oligonucleotide comprising first and second regions, and which is modified to prevent the initiation of DNA synthesis from its 3'-terminus. The "first region" of a promoter-provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 15, 20, 25, 30, 35, 40, 50 or more nucleotides in length. The "second region" comprises a promoter sequence for an RNA polymerase. A promoter-provider oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 provider" is a blocked promoter-provider oligonucleotide that provides an oligonucleotide sequence that is recognized by T7 RNA polymerase.

As used herein, a "terminating oligonucleotide" or "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

An "extender oligonucleotide" or "extend oligo" as used herein refers to an oligonucleotide that is the same sense as the T7 Provider and may act as a helper oligonucleotide that opens up structure or improves specificity.

As used herein, a "detection oligonucleotide" refers to a nucleic acid oligonucleotide that hybridizes specifically to a target sequence, including an amplified sequence, under conditions that promote nucleic acid hybridization, for detection of the target nucleic acid. By "probe" or "detection probe" is meant a molecule comprising an oligonucleotide having a base sequence partly or completely complementary to a region of a target sequence sought to be detected, so as to hybridize thereto under stringent hybridization conditions.

By "stable" or "stable for detection" is meant that the temperature of a reaction mixture is at least 2° C. below the melting temperature of a nucleic acid duplex.

By "amplification" or "nucleic acid amplification" is meant production of multiple copies of a target nucleic acid that contains at least a portion of the intended specific target nucleic acid sequence, as further described herein. The multiple copies may be referred to as amplicons or amplification products.

The term "amplicon" as used herein refers to the nucleic acid molecule generated during an amplification procedure that is complementary or homologous to a sequence contained within the target sequence.

By "preferentially hybridize" is meant that under stringent hybridization assay conditions, probes hybridize to their target sequences, or replicates thereof, to form stable probe: target hybrids, while at the same time formation of stable probe: non-target hybrids is minimized. Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "perfectly" complementary.

By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

As used herein, a "capture oligonucleotide" or "capture probe" refers to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (i.e., target-specific portion) and an immobilized probe-binding region, usually on the same oligomer, although the two regions may be present on two different oligomers joined together by one or more linkers.

As used herein, an "immobilized oligonucleotide", "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample.

As used herein, a "label" refers to a moiety or compound joined directly or indirectly to a probe that is detected or leads to a detectable signal.

As used herein, structures referred to as "molecular torches" are designed to include distinct regions of self-complementarity (coined "the target binding domain" and "the target closing domain") which are connected by a joining region and which hybridize to one another under predetermined hybridization assay conditions.

As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially-double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes other than RNAse H which possess the same or similar activity may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes which selectively degrade RNA target sequences or RNA products of the present invention will be readily apparent to those of ordinary skill in the art.

The term "specificity," in the context of an amplification system, is used herein to refer to the characteristic of an amplification system which describes its ability to distinguish between target and non-target sequences dependent on sequence and assay conditions. In terms of a nucleic acid amplification, specificity generally refers to the ratio of the number of specific amplicons produced to the number of side-products (i.e., the signal-to-noise ratio).

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, i.e., the ratio of specific amplicons to side-products.

As used herein, a "colony forming unit" ("CFU") is used as a measure of viable microorganisms in a sample. A CFU is an individual viable cell capable of forming on a solid medium a visible colony whose individual cells are derived by cell division from one parental cell. One CFU corresponds to ~1000 copies of rRNA.

As used herein, the term "TTime" is the threshold time or time of emergence of signal in a real-time plot of the assay data. TTime values estimate the time at which a particular threshold indicating amplicon production is passed in a real-time amplification reaction. TTime and an algorithm for calculating and using TTime values are described in Light et al., U.S. Pub. No. 2006/0276972, paragraphs [0517] through [0538], the disclosure of which is hereby incorporated by reference herein. A curve fitting procedure is applied to normalized and background-adjusted data. The curve fit is performed for only a portion of the data between a predetermined low bound and high bound. The goal, after finding the curve that fits the data, is to estimate the time corresponding to the point at which the curve or a projection thereof intersects a predefined threshold value. In one embodiment, the threshold for normalized data is 0.11. The high and low bounds are determined empirically as that range over which curves fit to a variety of control data sets exhibit the least variability in the time associated with the given threshold value. For example, in one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve y=mx+b are determined for the fitted curve. With that information, TTime can be determined as follows:

$$TTime=(Threshold-b)/m$$

As used herein, the term "relative fluorescence unit" ("RFU") is an arbitrary unit of measurement of fluorescence intensity. RFU varies with the characteristics of the detection means used for the measurement.

As used herein, the term "real-time TMA" refers to single-primer transcription-mediated amplification ("TMA") of target nucleic acid that is monitored by real-time detection means.

BRIEF DESCRIPTION OF THE DRAWINGS

FIG. 2 shows *Salmonella enterica* sbsp *enterica* sv Enteritidis GP60 (ATCC13076) "350 region" sequence (SEQ ID NO:150) corresponding to nucleotides 150-425 of *E. coli* 23s rRNA sequence.

DETAILED DESCRIPTION OF THE INVENTION

Figure 1A:
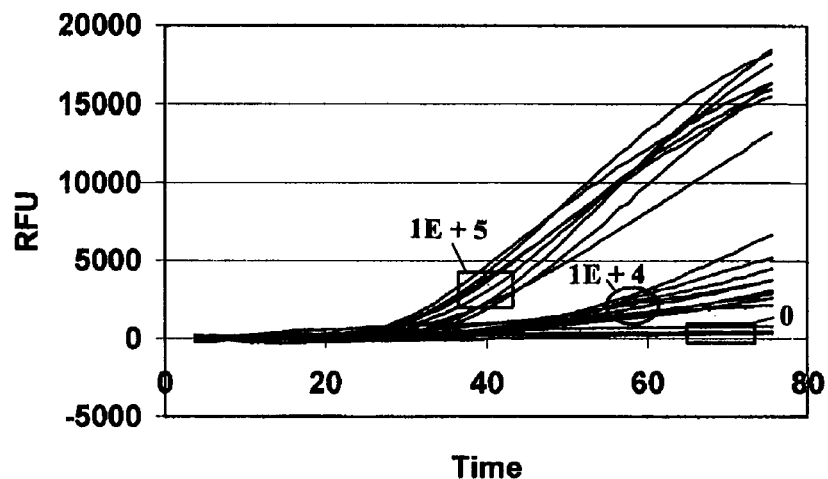
FIG. 1 illustrates real-time amplification charts of analyte showing (A) "Poor" and (B) "Good" assay performance of different combinations of amplification and detection oligonucleotides. The analyte used was purified *Salmonella enterica* rRNA and the charts show multiple replicates of the analyte at 0, 1 E+4, and 1 E+5 copies.

In certain aspects and embodiments, the invention relates to compositions, methods and kits for the identification, detection, and/or quantitation of *Salmonella*, which may be present either alone or as a component, large or small, of a homogeneous or heterogeneous mixture of nucleic acids in a sample taken for testing, e.g., for diagnostic testing, for screening of blood products, for microbiological detection in bioprocesses, food, water, industrial or environmental samples, and for other purposes. Specific methods, compositions, and kits as disclosed herein provide improved sensitivity, specificity, or speed of detection in the amplification-based detection of *Salmonella*. *Salmonella* ribosomal RNA is very closely related to *E. coli, Shigella* sp., *Citrobacter* sp., *Enterobacter* sp and other potential enteric bacteria. Accordingly, in certain embodiments of the invention, the *Salmonella* assay identifies rRNA sequences common to nearly all species, subspecies and serovars of the *Salmonella* genus, and differentiates *Salmonella* from other enteric bacteria. A useful region for such differentiation is the 350 region of the 23S rRNA.

As a result of extensive analyses of amplification oligonucleotides specific for *Salmonella*, the particular region of *Salmonella*, corresponding to the region of *E. coli* 23s rRNA reference sequence (accession no. AJ278710) from about 150-425 nucleotide bases (hereinafter referred to as the "350 region"), has been identified as a preferred target for amplification-based detection of *Salmonella*. Accordingly, the invention relates to methods of detection of *Salmonella* in a sample of interest, amplification oligonucleotides, compositions, reactions mixtures, kits, and the like.

The *Salmonella* genus assay detects ribosomal RNA sequences specific for known *Salmonella* species. It utilizes real-time TMA technology, where the target-specific sequence is amplified using reverse TMA and a fluorescent molecular torch is used to detect the amplified products as they are produced. Target detection is performed simultaneously with the amplification and detection of an internal control in order to confirm reliability of the result. The result of the assay consists of the classification of the sample as positive or negative for the presence or absence of *Salmonella*.

In one embodiment, the sample is a biopharmaceutical process (bioprocess) stream where *Salmonella* is a known or suspected contaminant. A "bioprocess," as used herein, refers generally to any process in which living cells or organisms, or components thereof, are present, either intended or unintended. For example, essentially any manufacturing or other process that employs one or more samples or sample streams, at least one of which contains living cells, organisms, or components thereof, or contains such cells, organisms or components as a result of unintended contamination, is considered a bioprocess. In many such processes it is desirable to have the ability to detect, identify and/or control the presence and/or sources of living cells, organisms or components thereof within a process. Using the methods disclosed herein, for example, the presence and/or sources of *Salmonella* in one or more bioprocess samples and/or streams may be monitored in a rapid and sensitive fashion.

Target Nucleic Acid/Target Sequence

Target nucleic acids may be isolated from any number of sources based on the purpose of the amplification assay being carried out. Sources of target nucleic acids include, but are not limited to, clinical specimens, e.g., blood, urine, saliva, feces, semen, or spinal fluid, from criminal evidence, from environmental samples, e.g., water or soil samples, from food, from industrial samples, from cDNA libraries, or from total cellular RNA. If necessary, target nucleic acids are made available for interaction with various oligonucleotides. This may include, for example, cell lysis or cell permeabilization to release the target nucleic acid from cells, which then may be followed by one or more purification steps, such as a series of isolation and wash steps. See, e.g., Clark et al., "Method for Extracting Nucleic Acids from a Wide Range of Organisms," U.S. Pat. No. 5,786,208, the contents of which are hereby incorporated by reference herein. This is particularly important where the sample may contain components that can interfere with the amplification reaction, such as, for example, heme present in a blood sample. See Ryder et al., "Amplification of Nucleic Acids from Mononuclear Cells Using Iron Complexing and Other Agents," U.S. Pat. No. 5,639,599, the contents of which are hereby incorporated by reference herein. Methods to prepare target nucleic acids from various sources for amplification are well known to those of ordinary skill in the art. Target nucleic acids may be purified to some degree prior to the amplification reactions described herein, but in other cases, the sample is added to the amplification reaction without any further manipulations.

As will be understood by those of ordinary skill in the art, "unique" sequences are judged from the testing environment. At least the sequences recognized by the detection probe should be unique in the environment being tested, but need not be unique within the universe of all possible sequences. Furthermore, even though the target sequence should contain a "unique" sequence for recognition by a detection probe, it is not always the case that the priming oligonucleotide and/or promoter oligonucleotide are recognizing "unique" sequences. In some embodiments, it may be desirable to choose a target sequence which is common to a family of related organisms. In other situations, a very highly specific target sequence, or a target sequence having at least a highly specific region recognized by the detection probe and amplification oligonucleotides, would be chosen so as to distinguish between closely related organisms, for example, between pathogenic and non-pathogenic *E. coli*. A target sequence may be of any practical length. A minimal target sequence includes the region which hybridizes to the priming oligonucleotide (or the complement thereof), the region which hybridizes to the hybridizing region of the promoter oligonucleotide (or the complement thereof), and a region used for detection, e.g., a region which hybridizes to a detection probe, The region which hybridizes with the detection probe may overlap with or be contained within the region which hybridizes with the priming oligonucleotide (or its complement) or the hybridizing region of the promoter oligonucleotide (or its complement). In addition to the minimal requirements, the optimal length of a target sequence depends on a number of considerations, for example, the amount of secondary structure, or self-hybridizing regions in the sequence. Typically, target sequences range from about 30 nucleotides in length to about 300 nucleotides in length. The optimal or preferred length may vary under different conditions which can be determined according to the methods described herein.

Nucleic Acid "Identity"

In certain embodiments, a nucleic acid comprises a contiguous base region that is at least 70%; or 75%; or 80%, or 85% or 90%, or 95%; or 100% identical to a contiguous base region of a reference nucleic acid. For short nucleic acids, the degree of identity between a base region of a "query" nucleic acid and a base region of a reference nucleic acid can be determined by manual alignment. "Identity" is determined by comparing just the sequence of nitrogenous bases, irrespective of the sugar and backbone regions of the nucleic acids being compared. Thus, the query:reference base sequence alignment may be DNA:DNA, RNA:RNA, DNA:RNA, RNA:DNA, or any combinations or analogs thereof. Equivalent RNA and DNA base sequences can be compared by converting U's (in RNA) to T's (in DNA).

Oligonucleotides & Primers

An oligonucleotide can be virtually any length, limited only by its specific function in the amplification reaction or in detecting an amplification product of the amplification reaction. However, in certain embodiments, preferred oligonucleotides will contain at least about 10; or 12; or 14; or 16; or 18; or 20; or 22; or 24; or 26; or 28; or 30; or 32; or 34; or 36; or 38; or 40; or 42; or 44; or 46; or 48; or 50; or 52; or 54; or 56 contiguous bases that are complementary to a region of the target nucleic acid sequence or its complementary strand. The contiguous bases are preferably at least about 80%, more preferably at least about 90%, and most preferably completely complementary to the target sequence to which the oligonucleotide binds. Certain preferred oligonucleotides are of lengths generally between about 10-100; or 12-75; or 14-50; or 15-40 bases long and optionally can include modified nucleotides.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide. Modifications include base modifications, sugar modifications or backbone modifications. Base modifications include, but are not limited to the use of the following bases in addition to adenine, cytidine, guanosine, thymine and uracil: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl substitution to the ribofuranosyl moiety. See Becker et al., U.S. Pat. No. 6,130,038. Other sugar modifications include, but are not limited to 2'-amino, 2'-fluoro, (L)-alpha-threofuranosyl, and pentopyranosyl modifications. The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine. DNA analogs having a pseudo peptide backbone are commonly referred to as "peptide nucleic acids" or "PNA" and are disclosed by Nielsen et al., "Peptide Nucleic Acids," U.S. Pat. No. 5,539,082. Other linkage modifications include, but are not limited to, morpholino bonds.

Non-limiting examples of oligonucleotides or oligos contemplated herein include nucleic acid analogs containing bicyclic and tricyclic nucleoside and nucleotide analogs (LNAs). See Imanishi et al., U.S. Pat. No. 6,268,490; and Wengel et al., U.S. Pat. No. 6,670,461.) Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions.

The design and sequence of oligonucleotides depend on their function as described below. Several variables to take into account include: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to initially screen large numbers of potential oligonucleotides.

The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer."

Blocking Moiety

A blocking moiety may be a small molecule, e.g., a phosphate or ammonium group, or it may be a modified nucleotide, e.g., a 3'2' dideoxynucleotide or 3' deoxyadenosine 5'-triphosphate (cordycepin), or other modified nucleotide. Additional blocking moieties include, for example, the use of a nucleotide or a short nucleotide sequence having a 3'-to-5' orientation, so that there is no free hydroxyl group at the 3'-terminus, the use of a 3' alkyl group, a 3' non-nucleotide moiety (see, e.g., Arnold et al., "Non-Nucleotide Linking Reagents for Nucleotide Probes," U.S. Pat. No. 6,031,091, the contents of which are hereby incorporated by reference herein), phosphorothioate, alkane-diol residues, peptide nucleic acid (PNA), nucleotide residues lacking a 3' hydroxyl group at the 3'-terminus, or a nucleic acid binding protein. Preferably, the 3'-blocking moiety comprises a nucleotide or a nucleotide sequence having a 3'-to-5' orientation or a 3' non-nucleotide moiety, and not a 3'2'-dideoxynucleotide or a 3' terminus having a free hydroxyl group. Additional methods to prepare 3'-blocking oligonucleotides are well known to those of ordinary skill in the art.

Priming Oligonucleotide or Primer

A priming oligonucleotide is extended by the addition of covalently bonded nucleotide bases to its 3'-terminus, which bases are complementary to the template. The result is a primer extension product. Suitable and preferred priming oligonucleotides are described herein. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer. By its very nature of being extended by a DNA polymerase, a priming oligonucleotide does not comprise a 3'-blocking moiety.

Promoter Oligonucleotide/Promoter Sequence

For binding, it was generally thought that such transcriptases required DNA which had been rendered double-stranded in the region comprising the promoter sequence via an extension reaction, however, it has been determined that efficient transcription of RNA can take place even under conditions where a double-stranded promoter is not formed through an extension reaction with the template nucleic acid. The template nucleic acid (the sequence to be transcribed) need not be double-stranded. Individual DNA-dependent RNA polymerases recognize a variety of different promoter sequences, which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

Terminating Oligonucleotide

A terminating oligonucleotide or "blocker" is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-methyl ribonucleotides. These modified nucleotides have demonstrated higher thermal stability of complementary duplexes. The 2'-O-methyl ribonucleotides also function to increase the resistance of oligonucleotides to exonucleases, thereby increasing the half-life of the modified oligonucleotides. See, e.g., Majlessi et al. (1988) *Nucleic Acids Res.* 26, 2224-9, the contents of which are hereby incorporated by reference herein. Other modifications as described elsewhere herein may be utilized in addition to or in place of 2'-O-methyl ribonucleotides. For example, a terminating oligonucleotide may comprise PNA or an LNA. See, e.g., Petersen et al. (2000) *J. Mol. Recognit.* 13, 44-53, the contents of which are hereby incorporated by reference herein. A terminating oligonucleotide typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. Suitable and preferred terminating oligonucleotides are described herein. It is noted that while a terminating oligonucleotide typically or necessarily includes a 3'-blocking moiety, "3'-blocked" oligonucleotides are not necessarily terminating oligonucleotides. Other oligonucleotides as disclosed herein, e.g., promoter oligonucleotides and capping oligonucleotides are typically or necessarily 3'-blocked as well.

Extender Oligonucleotide

An extender oligonucleotide hybridizes to a DNA template adjacent to or near the 3'-end of the first region of a promoter oligonucleotide. An extender oligonucleotide preferably hybridizes to a DNA template such that the 5'-terminal base of the extender oligonucleotide is within 3, 2 or 1 bases of the 3'-terminal base of a promoter oligonucleotide. Most preferably, the 5'-terminal base of an extender oligonucleotide is adjacent to the 3'-terminal base of a promoter oligonucleotide when the extender oligonucleotide and the promoter oligonucleotide are hybridized to a DNA template. To prevent extension of an extender oligonucleotide, a 3'-terminal blocking moiety is typically included.

Probe

As would be understood by someone having ordinary skill in the art, a probe comprises an isolated nucleic acid molecule, or an analog thereof, in a form not found in nature without human intervention (e.g., recombined with foreign nucleic acid, isolated, or purified to some extent). Probes may have additional nucleosides or nucleobases outside of the targeted region so long as such nucleosides or nucleobases do not substantially affect hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or may contain sequences which will confer a desired secondary or tertiary structure, such as a catalytic active site or a hairpin structure on the probe, on the target nucleic acid, or both.

The probes preferably include at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester. Certain probes as disclosed herein do not include a label. For example, non-labeled "capture" probes may be used to enrich for target sequences or replicates thereof, which may then be detected by a second "detection" probe. See, e.g., Weisburg et al., "Two-Step Hybridization and Capture of a Polynucleotide," U.S. Pat. No. 6,534,273, which is hereby incorporated by reference herein. While detection probes are typically labeled, certain detection technologies do not require that the probe be labeled. See, e.g., Nygren et al., "Devices and Methods for Optical Detection of Nucleic Acid Hybridization," U.S. Pat. No. 6,060,237.

Probes of a defined sequence may be produced by techniques known to those of ordinary skill in the art, such as by chemical synthesis, and by in vitro or in vivo expression from recombinant nucleic acid molecules. Preferably probes are 10 to 100 nucleotides in length, more preferably 12 to 50 bases in length, and even more preferably 18 to 35 bases in length.

Hybridize/Hybridization

Nucleic acid hybridization is the process by which two nucleic acid strands having completely or partially complementary nucleotide sequences come together under predetermined reaction conditions to form a stable, double-stranded hybrid. Either nucleic acid strand may be a deoxyribonucleic acid (DNA) or a ribonucleic acid (RNA) or analogs thereof. Thus, hybridization can involve RNA:RNA hybrids, DNA:DNA hybrids, RNA:DNA hybrids, or analogs thereof. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., Roger L. P. Adams et al., "The Biochemistry Of The Nucleic Acids" ($11^{th}$ ed. 1992).)

"Stringent" hybridization assay conditions refer to conditions wherein a specific detection probe is able to hybridize with target nucleic acids over other nucleic acids present in the test sample. It will be appreciated that these conditions may vary depending upon factors including the GC content and length of the probe, the hybridization temperature, the composition of the hybridization reagent or solution, and the degree of hybridization specificity sought. Specific stringent hybridization conditions are provided in the disclosure below.

Nucleic Acid Amplification

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos.

4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA. The ligase chain reaction (Weiss, R. 1991, Science 254: 1292), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product. Another method is strand displacement amplification (Walker, G. et al., 1992, Proc. Natl. Acad. Sci. USA 89:392-396; U.S. Pat. Nos. 5,270,184 and 5,455,166), commonly referred to as SDA, which uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315). Other amplification methods include: nucleic acid sequence based amplification (U.S. Pat. No. 5,130,238), commonly referred to as NASBA; one that uses an RNA replicase to amplify the probe molecule itself (Lizardi, P. et al., 1988, BioTechnol. 6: 1197-1202), commonly referred to as Q-β replicase; a transcription-based amplification method (Kwoh, D. et al., 1989, Proc. Natl. Acad. Sci. USA 86:1173-1177); self-sustained sequence replication (Guatelli, J. et al., 1990, Proc. Natl. Acad. Sci. USA 87: 1874-1878); and, transcription-mediated amplification (U.S. Pat. Nos. 5,480,784 and 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.).

In a preferred embodiment, *Salmonella* is detected by a transcription-based amplification technique. One preferred transcription-based amplification system is transcription-mediated amplification (TMA), which employs an RNA polymerase to produce multiple RNA transcripts of a target region. Exemplary TMA amplification methods are described in U.S. Pat. Nos. 5,480,784, 5,399,491, 7,374,885, and references cited therein, the contents of which are incorporated herein by reference in their entireties. TMA uses a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In one version of the TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce promoter-primer extension. From an unmodified promoter-primer, reverse transcriptase creates a cDNA copy of the target RNA, while RNase H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNase H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

Another version of TMA uses one primer and one or more additional amplification oligomers to amplify nucleic acids in vitro, making transcripts (amplicons) that indicate the presence of the target sequence in a sample (described in Becker et al., U.S. Pat. No. 7,374,885, the details of which are hereby incorporated by reference herein). Briefly, the single-primer TMA method uses a primer (or "priming oligomer"), a modified promoter oligomer (or "promoter-provider") that is modified to prevent the initiation of DNA synthesis from its 3' end (e.g., by including a 3'-blocking moiety) and, optionally, a binding molecule (e.g., a 3'-blocked extender oligomer) to terminate elongation of a cDNA from the target strand. As referred to herein, a "T7 provider" is a blocked promoter-provider oligonucleotide that provides an oligonucleotide sequence that is recognized by T7 RNA polymerase. This method synthesizes multiple copies of a target sequence and includes the steps of treating a target RNA that contains a target sequence with a priming oligomer and a binding molecule, where the primer hybridizes to the 3' end of the target strand. RT initiates primer extension from the 3' end of the primer to produce a cDNA which is in a duplex with the target strand (e.g., RNA:cDNA). When a binding molecule, such as a 3' blocked extender oligomer, is used in the reaction, it binds to the target nucleic acid adjacent near the 5' end of the target sequence. That is, the binding molecule binds to the target strand next to the 5' end of the target sequence to be amplified. When the primer is extended by DNA polymerase activity of RT to produce cDNA, the 3' end of the cDNA is determined by the position of the binding molecule because polymerization stops when the primer extension product reaches the binding molecule bound to the target strand. Thus, the 3' end of the cDNA is complementary to the 5' end of the target sequence.

The RNA:cDNA duplex is separated when RNase (e.g., RNase H of RT) degrades the RNA strand, although those skilled in the art will appreciate that any form of strand separation may be used. Then, the promoter-provider oligomer hybridizes to the cDNA near the 3' end of the cDNA strand. The promoter-provider oligomer includes a 5' promoter sequence for an RNA polymerase and a 3' region complementary to a sequence in the 3' region of the cDNA. The promoter-provider oligomer also has a modified 3' end that includes a blocking moiety that prevents initiation of DNA synthesis from the 3' end of the promoter-provider oligomer. In the promoter-provider: cDNA duplex, the 3'-end of the cDNA is extended by DNA polymerase activity of RT using the promoter oligomer as a template to add a promoter sequence to the cDNA and create a functional double-stranded promoter. An RNA polymerase specific for the promoter sequence then binds to the functional promoter and transcribes multiple RNA transcripts complementary to the cDNA and substantially identical to the target region sequence that was amplified from the initial target strand. The resulting amplified RNA can then cycle through the process again by binding the primer and serving as a template for further cDNA production, ultimately producing many amplicons from the initial target nucleic acid present in the sample. Some embodiments of the single-primer transcription-associated amplification method do not include the binding molecule and, therefore, the cDNA product made from the primer has an indeterminate 3' end, but the amplification steps proceed substantially as described above for all other steps.

Suitable amplification conditions can be readily determined by a skilled artisan in view of the present disclosure. "Amplification conditions" as disclosed herein refer to conditions which permit nucleic acid amplification. Amplification conditions may, in some embodiments, be less stringent than "stringent hybridization conditions" as described herein. Oligonucleotides used in the amplification reactions as disclosed herein may be specific for and hybridize to their intended targets under amplification conditions, but in certain embodiments may or may not hybridize under more stringent hybridization conditions. On the other hand, detection probes generally hybridize under stringent hybridization conditions. While the Examples section infra provides preferred amplification conditions for amplifying target nucleic acid sequences, other acceptable conditions to carry out nucleic acid amplifications could be easily ascertained by someone having ordinary skill in the art depending on the particular method of amplification employed.

The amplification methods as disclosed herein, in certain embodiments, also preferably employ the use of one or more other types of oligonucleotides that are effective for improving the sensitivity, selectivity, efficiency, etc., of the amplification reaction. These may include, for example, terminating oligonucleotides, extender or helper oligonucleotides, and the like.

Target Capture

In certain embodiments, it may be preferred to purify or enrich a target nucleic acid from a sample prior to amplification, for example using a target capture approach. "Target capture" (TC) refers generally to capturing a target polynucleotide onto a solid support, such as magnetically attractable particles, wherein the solid support retains the target polynucleotide during one or more washing steps of the target polynucleotide purification procedure. In this way, the target polynucleotide is substantially purified prior to a subsequent nucleic acid amplification step. Numerous target capture methods are known and suitable for use in conjunction with the methods described herein.

Any support may be used, e.g., matrices or particles free in solution, which may be made of any of a variety of materials, e.g., nylon, nitrocellulose, glass, polyacrylate, mixed polymers, polystyrene, silane polypropylene, or metal. Illustrative examples use a support that is magnetically attractable particles, e.g., monodisperse paramagnetic beads (uniform size.+−.5%) to which an immobilized probe is joined directly (e.g., via covalent linkage, chelation, or ionic interaction) or indirectly (e.g., via a linker), where the joining is stable during nucleic acid hybridization conditions.

For example, one illustrative approach, as described in U.S. Patent Application Publication No 20060068417, uses at least one capture probe oligonucleotide that contains a target-complementary region and a member of a specific binding pair that attaches the target nucleic acid to an immobilized probe on a capture support, thus forming a capture hybrid that is separated from other sample components before the target nucleic acid is released from the capture support.

In another illustrative method, Weisburg et al., in U.S. Pat. No. 6,110,678, describe a method for capturing a target polynucleotide in a sample onto a solid support, such as magnetically attractable particles, with an attached immobilized probe by using a capture probe and two different hybridization conditions, which preferably differ in temperature only. The two hybridization conditions control the order of hybridization, where the first hybridization conditions allow hybridization of the capture probe to the target polynucleotide, and the second hybridization conditions allow hybridization of the capture probe to the immobilized probe. The method may be used to detect the presence of a target polynucleotide in a sample by detecting the captured target polynucleotide or amplified target polynucleotide.

Another illustrative target capture technique (U.S. Pat. No. 4,486,539) involves a hybridization sandwich technique for capturing and for detecting the presence of a target polynucleotide. The technique involves the capture of the target polynucleotide by a probe bound to a solid support and hybridization of a detection probe to the captured target polynucleotide. Detection probes not hybridized to the target polynucleotide are readily washed away from the solid support. Thus, remaining label is associated with the target polynucleotide initially present in the sample.

Another illustrative target capture technique (U.S. Pat. No. 4,751,177) involves a method that uses a mediator polynucleotide that hybridizes to both a target polynucleotide and to a polynucleotide fixed on a solid support. The mediator polynucleotide joins the target polynucleotide to the solid support to produce a bound target. A labeled probe can be hybridized to the bound target and unbound labeled pro can be washed away from the solid support.

Yet another illustrative target capture technique is described in U.S. Pat. Nos. 4,894,324 and 5,288,609, which describe a method for detecting a target polynucleotide. The method utilizes two single-stranded polynucleotide segments complementary to the same or opposite strands of the target and results in the formation of a double hybrid with the target polynucleotide. In one embodiment, the hybrid is captured onto a support.

In another illustrative target capture technique, EP Pat. Pub. No. 0 370 694, methods and kits for detecting nucleic acids use oligonucleotide primers labeled with specific binding partners to immobilize primers and primer extension products. The label specifically complexes with its receptor which is bound to a solid support.

The above capture techniques are illustrative only, and not limiting. Indeed, essentially any technique available to the skilled artisan may be used provided it is effective for purifying a target nucleic acid sequence of interest prior to amplification.

Nucleic Acid Detection

Essentially any labeling and/or detection system that can be used for monitoring specific nucleic acid hybridization can be used in conjunction to detect *Salmonella* amplicons. Many such systems are known and available to the skilled artisan, illustrative examples of which are briefly discussed below.

Detection systems typically employ a detection oligonucleotide of one type or another in order to facilitate detection of the target nucleic acid of interest. Detection may either be direct (i.e., probe hybridized directly to the target) or indirect (i.e., a probe hybridized to an intermediate structure that links the probe to the target). A probe's target sequence generally refers to the specific sequence within a larger sequence which the probe hybridizes specifically. A detection probe may include target-specific sequences and other sequences or structures that contribute to the probe's three-dimensional structure, depending on whether the target sequence is present (e.g., U.S. Pat. Nos. 5,118,801, 5,312,728, 6,835,542, and 6,849,412).

Any of a number of well known labeling systems may be used to facilitate detection. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent or chemiluminescent compound), and fluorescent compound. Preferred embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 6,004,745, 5,656,207 and 5,658,737). Preferred homogeneous detectable labels include chemiluminescent compounds, more preferably acridinium ester ("AE") compounds, such as standard AE or AE derivatives which are well known (U.S. Pat. Nos. 5,656,207, 5,658,737, and 5,948,899). Methods of synthesizing labels, attaching labels to nucleic acid, and detecting signals from labels are well known (e.g., Sambrook et al., Molecular Cloning, A Laboratory Manual, 2nd ed. (Cold Spring Harbor Laboratory Press, Cold Spring Harbor, N.Y., 1989) at Chapter. 10, and U.S. Pat. Nos. 6,414,152, 5,185,439, 5,658,737, 5,656,207, 5,547,842, 5,639,604, 4,581,333, and 5,731,148). Preferred methods of linking an AE compound to a nucleic acid are known (e.g., U.S. Pat. No. 5,585,481 and U.S. Pat. No. 5,639,604, see column 10, line 6 to column 11, line 3, and Example 8). Preferred AE labeling positions are a probe's central region and near a region of A/T base pairs, at a probe's 3' or 5' terminus, or at or near a mismatch site with a known sequence that is the probe should not detect compared to the desired target sequence.

In a preferred embodiment, oligonucleotides exhibiting at least some degree of self-complementarity are desirable to facilitate detection of probe:target duplexes in a test sample without first requiring the removal of unhybridized probe prior to detection. By way of example, when exposed to denaturing conditions, the two complementary regions of a molecular torch, which may be fully or partially complementary, melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., a fluorescent/quencher pair) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference herein.

Another example of a self-complementary hybridization assay probe that may be used is a structure commonly referred to as a "molecular beacon." Molecular beacons comprise nucleic acid molecules having a target complementary sequence, an affinity pair (or nucleic acid arms) that holds the probe in a closed conformation in the absence of a target nucleic acid sequence, and a label pair that interacts when the probe is in a closed conformation. Hybridization of the molecular beacon target complementary sequence to the target nucleic acid separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference herein. Molecular beacons useful for detecting specific nucleic acid sequences may be created by appending to either end of one of the probe sequences disclosed herein, a first nucleic acid arm comprising a fluorophore and a second nucleic acid arm comprising a quencher moiety. In this configuration, *Salmonella*-specific probe sequences may serve as the target-complementary "loop" portion of the resulting molecular beacon.

Molecular beacons are preferably labeled with an interactive pair of detectable labels. Preferred detectable labels interact with each other by FRET or non-FRET energy transfer mechanisms. Fluorescence resonance energy transfer (FRET) involves the radiationless transmission of energy quanta from the site of absorption to the site of its utilization in the molecule or system of molecules by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close such that energy emitted by one label can be received or absorbed by the second label, whether by a FRET or non-FRET mechanism, the two labels are said to be in an "energy transfer relationship." This is the case, for example, when a molecular beacon is maintained in the closed state by formation of a stem duplex and fluorescent emission from a fluorophore attached to one arm of the molecular beacon is quenched by a quencher moiety on the other arm.

Illustrative label moieties for the molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same molecular beacon is in the open state and is stimulated by an appropriate frequency of light, the fluorophore and the quencher moieties are sufficiently separated from each other such that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used, making no attempt to distinguish FRET from non-FRET pairs, include fluorescein/tetramethylrhodamine, IAEDANS/fluorescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2, and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the Black Hole Quencher moieties, which are available from Biosearch Technologies, Inc. (Novato, Calif.).

Synthetic techniques and methods of attaching labels to nucleic acids and detecting labels are well known in the art (see, e.g., Sambrook et al., Molecular Cloning: A Laboratory Manual, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. Nos. 5,185,439 and 6,004,745; Kourilsky et al., U.S. Pat. No. 4,581,333; and, Becker et al., U.S. Pat. No. 5,731,148).

Preferred *Salmonella* Oligonucicotides and Oligonucleotide Sets

As described herein, preferred sites for amplifying and detecting *Salmonella* nucleic acids as disclosed herein have been found to reside in the 350 region of *Salmonella* 23S rRNA. Moreover, particularly preferred oligonucleotides and oligonucleotide sets within this region have been identified for amplifying *Salmonella* 23S with improved sensitivity, selectivity and specificity. It will be understood that the oligonucleotides disclosed herein are capable of hybridizing to a *Salmonella* target sequence with high specificity and, as a result, are capable of participating in a nucleic acid amplification reaction that can be used to detect the presence and/or levels of *Salmonella* in a sample and distinguish it from the presence of other enteric bacteria.

For example, in one embodiment, the amplification oligonucleotides comprise a first oligonucleotide and a second oligonucleotide, wherein the first and second oligonucleotides target the 350 region of the *Salmonella* 23s rRNA with a high degree of specificity. Of course, it will be understood, when discussing the amplification oligonucleotides disclosed herein that the first and second oligonucleotides used in an amplification reaction have specificity for opposite strands of the target nucleic acid sequence to be amplified.

The amplification oligonucleotides disclosed herein are particularly effective for amplifying a target nucleic acid sequence of *Salmonella* in a transcription-based amplification reaction, preferably a real-time transcription-mediated amplification (TMA) reaction.

It will be understood that in addition to the particular T7 provider oligonucleotides and primer oligonucleotides used in the amplification reaction, additional oligonucleotides will also generally be employed in conjunction with the amplification reaction. For example, in certain embodiments, the amplification reactions will also employ the use of one or more of a detection oligonucleotide (e.g., a torch oligonucleotide), and a blocker oligonucleotide.

Table 1 presents specific examples of T7 Provider oligonucleotides, Primer oligonucleotides, and other ancillary oligonucleotides (e.g., Blocker, Torch, and Target Capture oligonucleotides) that have been identified by the invention.

TABLE 1

Examples of Preferred Oligonucleotides

| Use | SEQ ID NO: | Sequence (5'-3') |
|---|---|---|
| T7 Provider | SEQ ID NO: 1 | AATTTAATACGACTCACTATAGGGAGA-ATCAGCTTGTGTGTTAGTGGAAGC-X |
| T7 Provider | SEQ ID NO: 2 | AATTTAATACGACTCACTATAGGGAGA-AGTGGAAGCGTCTGGAAAGGCGCG-X |
| T7 Provider | SEQ ID NO: 3 | AATTTAATACGACTCACTATAGGGAGA-GTTAGTGGAAGCGTCTGGAAAGGC-X |

TABLE 1-continued

Examples of Preferred Oligonucleotides

| Use | SEQ ID NO: | Sequence (5'-3') |
|---|---|---|
| T7 Provider | SEQ ID NO: 4 | AATTTAATACGACTCACTATAGGGAGA-TAGTGGAAGCGTCTGGAAAGGCGC-X |
| T7 Provider | SEQ ID NO: 5 | AATTTAATACGACTCACTATAGGGAGA-GGAAGCGTCTGGAAAGGCGCGCGA-X |
| T7 Provider | SEQ ID NO: 6 | AATTTAATACGACTCACTATAGGGAGA-CCAGAGCCTGAATCAGCTTGTGTG-X |
| T7 Provider | SEQ ID NO: 7 | AATTTAATACGACTCACTATAGGGAGA-CGTGTGTGTTAGTGGAAGCGTCTGGAA-X |
| T7 Provider | SEQ ID NO: 8 | AATTTAATACGACTCACTATAGGGAGA-CGTGTGTGTTAGTGGAAGCGTCTGGA-X |
| T7 Provider | SEQ ID NO: 9 | AATTTAATACGACTCACTATAGGGAGA-CGTGTGTGTTAGTGGAAGCGTCTGG-X |
| T7 Provider | SEQ ID NO: 10 | AATTTAATACGACTCACTATAGGGAGA-CCACAAATCAGCTTGTGTGTTAGTGGAAGC-X |
| T7 Provider | SEQ ID NO: 11 | AATTTAATACGACTCACTATAGGGAGA-CCACAACGGTTTATCAGCTTGTGTGTTAGTGGAAGC-X |
| T7 Provider | SEQ ID NO: 12 | AATTTAATACGACTCACTATAGGGAGA-ATCAGCATGTGTGTTAGTGGAAGC-X |
| T7 Provider | SEQ ID NO: 13 | AATTTAATACGACTCACTATAGGGAGA-CCACAACGGTTTATCAGCATGTGTGTTAGTGGAAGC-X |
| T7 Provider | SEQ ID NO: 14 | AATTTAATACGACTCACTATAGGGAGA-ATCAGCGTGTGTGTTAGTGGAAGC-X |
| T7 Provider | SEQ ID NO: 15 | AATTTAATACGACTCACTATAGGGAGA-ATCAGCTGGTGTGTTAGTGGAAGC-X |
| T7 Provider | SEQ ID NO: 16 | AATTTAATACGACTCACTATAGGGAGA-CCACAACGGTTTATCAGCTGGTGTGTTAGTGGAAGC-X |
| T7 Provider | SEQ ID NO: 17 | AATTTAATACGACTCACTATAGGGAGA-ATCAGCAGGTGTGTTAGTGGAAGC-X |
| T7 Provider | SEQ ID NO: 18 | AATTTAATACGACTCACTATAGGGAGA-CCACAACGGTTTATCAGCAGGTGTGTTAGTGGAAGC-X |
| T7 Provider | SEQ ID NO: 19 | AATTTAATACGACTCACTATAGGGAGA-ATCAGCTTGTGTGTTAGTGGAAGCG-X |
| T7 Provider | SEQ ID NO: 20 | AATTTAATACGACTCACTATAGGGAGA-ATCAGCTTGTGTGTTAGTGGAAGCGT-X |
| T7 Provider | SEQ ID NO: 21 | AATTTAATACGACTCACTATAGGGAGA-ATCAGCTTGTGTGTTAGTGGAAGCGTC-X |
| T7 Provider | SEQ ID NO: 22 | AATTTAATACGACTCACTATAGGGAGA-ATCAGCTTGTGTGTTAGTGGAAGCGTCTG-X |
| T7 Provider | SEQ ID NO: 23 | AATTTAATACGACTCACTATAGGGAGA-ATCAGCTTGTGTGTTAGTGGAAGCGTCTGG-X |
| T7 Provider | SEQ ID NO: 24 | AATTTAATACGACTCACTATAGGGAGA-ATCAGCTTGTGTGTTAGTGGAAGCGTCTGGA-X |
| T7 Provider | SEQ ID NO: 25 | AATTTAATACGACTCACTATAGGGAGA-ATCAGCTTGTGTGTTAGTGGAAGCGTCTGGAA-X |
| T7 Provider | SEQ ID NO: 26 | AATTTAATACGACTCACTATAGGGAGA-ATCAGCTTGTGTGTTAGTGGAAGCGTCT-X |

TABLE 1-continued

Examples of Preferred Oligonucleotides

| Use | SEQ ID NO: | Sequence (5'-3') |
|---|---|---|
| T7 Provider | SEQ ID NO: 27 | AATTTAATACGACTCACTATAGGGAGA-ATCAGCACGTGTGTTAGTGGAAGC-X |
| T7 Provider | SEQ ID NO: 28 | AATTTAATACGACTCACTATAGGGAGA-ATCAGCATGCGTGTTAGTGGAAGC-X |
| T7 Provider | SEQ ID NO: 29 | AATTTAATACGACTCACTATAGGGAGA-ATCAGCATGTGCGTTAGTGGAAGC-X |
| T7 Provider | SEQ ID NO: 30 | AATTTAATACGACTCACTATAGGGAGA-ATCAGCATGTGTGCTAGTGGAAGC-X |
| T7 Provider | SEQ ID NO: 31 | AATTTAATACGACTCACTATAGGGAGA-ATCAGCATGTGTGTTAGCGGAAGC-X |
| T7 Provider | SEQ ID NO: 32 | AATTTAATACGACTCACTATAGGGAGA-ATCAGCAAGTGTGTTAGTGGAAGC-X |
| T7 Provider | SEQ ID NO: 33 | AATTTAATACGACTCACTATAGGGAGA-CCACAAATCAGCTTGTGTGTTAGTGGAAGCGTCT-X |
| T7 Provider | SEQ ID NO: 34 | AATTTAATACGACTCACTATAGGGAGA-CCACAACGGTTTATCAGCTTGTGTGTTAGTGGAAGCGTCT-X |
| Primer | SEQ ID NO: 35 | TCACAGCACATGCGC |
| Primer | SEQ ID NO: 36 | CTCACAGCACATGCGC |
| Primer | SEQ ID NO: 37 | GCTCACAGCACATGCGC |
| Primer | SEQ ID NO: 38 | AGCTCACAGCACATGCGC |
| Primer | SEQ ID NO: 39 | AGCTCACAGCACATcCGC |
| Primer | SEQ ID NO: 40 | CGAGCTCACAGCACATGCGC |
| Primer | SEQ ID NO: 41 | cgagCTCACAGCACATGCGC |
| Primer | SEQ ID NO: 42 | cgagCTCACAGCACATCCGC |
| Primer | SEQ ID NO: 43 | ATCGAGCTCACAGCACATGCGC |
| Primer | SEQ ID NO: 44 | aucgAGCTCACAGCACATGCGC |
| Primer | SEQ ID NO: 45 | aucgAGCTCACAGCACATCCGC |
| Primer | SEQ ID NO: 46 | acucATCGAGCTCACAGCACATGCGCT |
| Primer | SEQ ID NO: 47 | CGAGCTCACAGCACATCCGC |
| Primer | SEQ ID NO: 48 | ATCGAGCTCACAGCACATCCGC |
| Primer | SEQ ID NO: 49 | AGCTCACAGCAGATCCGC |
| Primer | SEQ ID NO: 50 | AGCTCACAGCACCTCCGC |

TABLE 1-continued

Examples of Preferred Oligonucleotides

| Use | SEQ ID NO: | Sequence (5'-3') |
|---|---|---|
| Primer | SEQ ID NO: 51 | AGCTCACAGCAGCTCCGC |
| Primer | SEQ ID NO: 52 | GCTCACAGCACATGCGCTTTTGTGTACG |
| Primer | SEQ ID NO: 53 | CTCATCGAGCTCACAGCACATGCGCTTTTGTG |
| Primer | SEQ ID NO: 54 | CCCTACTCATCGAGCTCACAGCAC |
| Primer | SEQ ID NO: 55 | GGATACCACGTGTCCCGCCCTACTC |
| Primer | SEQ ID NO: 56 | CGAGCTCACAGCACATGCGCTTTTGTGTACG |
| Primer | SEQ ID NO: 57 | AGCTCACAGCACATGCCC |
| Primer | SEQ ID NO: 58 | CGAGCTCACAGCACACGCGCTTTTGTGTACG |
| Blocker | SEQ ID NO: 59 | cugauucaggcucugggcucc-X |
| Blocker | SEQ ID NO: 60 | ccacuaacacacacgcugau-X |
| Blocker | SEQ ID NO: 61 | cuaacacacacgcugauucagg-X |
| Blocker | SEQ ID NO: 62 | cacuaacacacacgcugauucagg-X |
| Blocker | SEQ ID NO: 63 | cuuccacuaacacacacgcu |
| Blocker | SEQ ID NO: 64 | ucugggcuccuccccguucg |
| Blocker | SEQ ID NO: 65 | acacgcugauucaggcucugg-X |
| Torch | SEQ ID NO: 66 | ggcugucacccuguau9cagcc |
| Torch | SEQ ID NO: 67 | cgcgc9ugucacccuguaucgcgcg |
| Torch | SEQ ID NO: 68 | cacccuguaucgcgc9gggug |
| Torch | SEQ ID NO: 69 | cacccuguaucgcgcgccuuuc9gggug |
| Torch | SEQ ID NO: 70 | cccc9gcuuuuguguacgggg |
| Target Capture | SEQ ID NO: 71 | ccgguucgccucauuaacc-TTTAAAAAAAAAAAAAAAAAAAAAAAAAAAA |
| Target Capture | SEQ ID NO: 72 | ccucggggguacuuagauguuuc-TTTAAAAAAAAAAAAAAAAAAAAAAAAAAAA |
| Target Capture | SEQ ID NO: 73 | ggaaucucgguugauuucuuuucc-TTTAAAAAAAAAAAAAAAAAAAAAAAAAAAA |
| Target Capture | SEQ ID NO: 74 | ccguucgcucgccgcuacug-TTTAAAAAAAAAAAAAAAAAAAAAAAAAAAA |
| Target Capture | SEQ ID NO: 75 | cugauucaggcucugggcucc-TTTAAAAAAAAAAAAAAAAAAAAAAAAAAAA |

TABLE 1-continued

Examples of Preferred Oligonucleotides

| Use | SEQ ID NO: | Sequence (5'-3') |
|---|---|---|
| Target Capture | SEQ ID NO: 76 | cagacaggataccacgtgtcc-TTTAAAAAAAAAAAAAAAAAAAAAAAAAAAAA |
| Target Capture | SEQ ID NO: 77 | cccatattcagacaggatacc-TTTAAAAAAAAAAAAAAAAAAAAAAAAAAAAA |

Lower case 2'-O--methyl RNA
X is a blocking moiety (e.g., reverse(3'-5') C blocked)
9 is a non-nucleotide (triethylene glycol) linker joining region, and
5'-fluorescein ("F") fluorophore and 3'-dabsyl ("D") quencher moieties were
attached to the torch oligonucleotides In addition, Table 2 identifies two particularly preferred oligonucleotide sets for use in the compositions, kits and methods as disclosed herein.

TABLE 2

Example of Two Preferred Oligonucleotide Sets

| Oligonucleotide Set | Description | Oligonucleotide |
|---|---|---|
| Set #1 | T7 Provider | SEQ ID NO: 17 |
|  | Blocker | SEQ ID NO: 59 |
|  | Primer | SEQ ID NO: 50 |
|  | Torch | SEQ ID NO: 66 |
| Set #2 | T7 Provider | SEQ ID NO: 26 |
|  | Blocker | SEQ ID NO: 59 |
|  | Primer | SEQ ID NO: 49 |
|  | Torch | SEQ ID NO: 66 |

While specifically preferred amplification oligonucleotides derived from the 350 region have been identified, which result in superior assay performance, it will be recognized that other oligonucleotides derived from the 350 region and having insubstantial modifications from those specifically described herein may also be used, provided the same or similar performance objectives are achieved. For example, oligonucleotides derived from the 350 region and useful in the amplification reactions as disclosed herein can have different lengths from those identified herein, provided it does not substantially affect amplification and/or detection procedures. These and other routine and insubstantial modifications to the preferred oligonucleotides can be carried out using conventional techniques, and to the extent such modifications maintain one or more advantages provided herein they are considered within the spirit and scope of the invention.

The general principles as disclosed herein may be more fully appreciated by reference to the following non-limiting Examples.

EXAMPLES

Examples are provided below illustrating certain aspects and embodiments. The examples below are believed to accurately reflect the details of experiments actually performed, however, it is possible that some minor discrepancies may exist between the work actually performed and the experimental details set forth below which do not affect the conclusions of these experiments or the ability of skilled artisans to practice them. Skilled artisans will appreciate that these examples are not intended to limit the invention to the specific embodiments described therein. Additionally, those skilled in the art, using the techniques, materials and methods described herein, could easily devise and optimize alternative amplification systems for carrying out these and related methods while still being within the spirit and scope of the present invention.

Unless otherwise indicated, oligonucleotides and modified oligonucleotides in the following examples were synthesized using standard phosphoramidite chemistry, various methods of which are well known in the art. See e.g., Carruthers, et al., 154 Methods in Enzymology, 287 (1987), the contents of which are hereby incorporated by reference herein. Unless otherwise stated herein, modified nucleotides were 2'-O-methyl ribonucleotides, which were used in the synthesis as their phosphoramidite analogs. For blocked oligonucleotides used in single-primer amplification (Becker et al., U.S. Pat. No. 7,374,885, hereby incorporated by reference herein), the 3'-terminal blocking moiety consisted of a "reversed C" 3'-to-3' linkage prepared using 3'-dimethyltrityl-N-benzoyl-2'-deoxycytidine, 5'-succinoyl-long chain alkylamino-CPG (Glen Research Corporation, Cat. No. 20-0102-01). Molecular torches (see Becker et al., U.S. Pat. No. 6,849,412, hereby incorporated by reference herein) were prepared using a C9 non-nucleotide (triethylene glycol) linker joining region (Spacer Phosphoramidite 9, Glen Research Corporation, Cat. No. 10-1909-xx), 5'-fluorescein ("F") fluorophore and 3'-dabsyl ("D") quencher moieties attached to the oligonucleotide by standard methods.

Figure 1B:
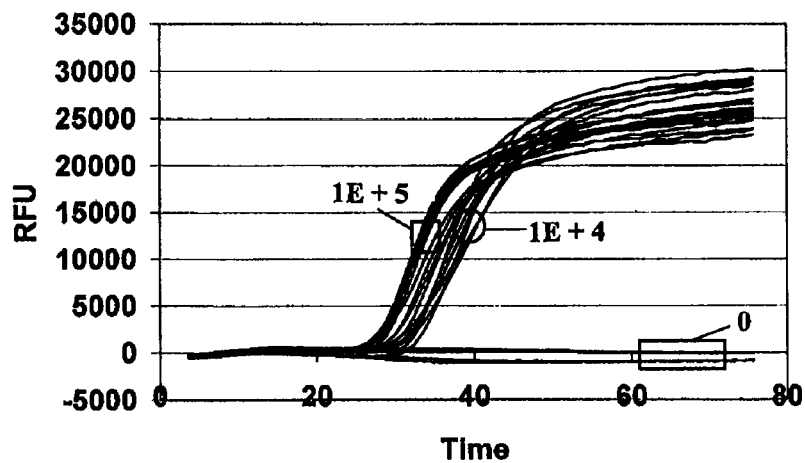

As set forth in the examples below, analyses of a wide variety of amplification reagents and conditions has led to the development of a highly sensitive and selective amplification process for the detection of Salmonella. The raw real-time amplification assay charts of multiple replicates of analyte at different target concentrations (see, e.g., FIG. 1) were utilized to assess the quality of the oligonucleotide sets. The data from the real-time assays were collected and analyzed to calculate TTime values and RFU range for presentation of data herein below.

Example 1

Description of Illustrative Assay Reagents and Protocols

The following example describes typical assay reagents, protocols, conditions and the like used in the real-time TMA experiments described herein. Unless specified to the contrary, reagent preparation, equipment preparation and assay protocols were performed essentially as set forth below.

A. Reagents and Samples
   1. Amplification Reagent.
   The "Amplification Reagent" or "Amp Reagent" comprised approximate concentrations of the following components: 0.5 mM dATP, 0.5 mM dCTP, 0.5 mM dGTP, 0.5 mM dTTP, 10 mM ATP, 2 mM CTP, 2 mM GTP, 12.7 mM UTP, 30 mM $MgCl_2$, and 33 mM KCl in 50 mM HEPES buffer at pH 7.7. Primers and other oligonucleotides were added to the Amp Reagent.
   2. Enzyme Reagent.
   The "Enzyme Reagent" comprised approximate concentrations of the following components: 1180 RTU/µL Moloney murine leukemia virus ("MMLV") reverse transcriptase ("RT") and 260 PU/µL T7 RNA polymerase in 75 mM HEPES buffer containing 120 mM KCl, 10% TRITON® X-100, 160 mM N-acetyl-L-cysteine, and 1 mM EDTA at pH 7.0, where one RTU of RT activity incorporates 1 nmol of dT into a substrate in 20 minutes at 37° C. and one PU of T7 RNA polymerase activity produces 5 fmol of RNA transcript in 20 minutes at 37° C.
   3. Wash Solution.
   The "Wash Solution" comprised 0.1% (w/v) sodium dodecyl sulfate, 150 mM NaCl and 1 mM EDTA in 10 mM HEPES buffer at pH to 7.5.
   4. Target Capture Reagent.
   The "Target Capture Reagent" (TCR) comprised approximate concentrations of the following components: 60 pmol/mL each of one or more capture probes having a $dT_3dA_{30}$ tail and an optional capture helper probe, 250 to 300 ug/mL paramagnetic oligo-$(dT)_{14}$ microparticles (Seradyn), 250 mM HEPES, 100 mM EDTA and 1.88 M LiCl at pH 6.5.
   5. Lysis Reagent.
   The "Lysis Buffer" comprised 1% lithium lauryl sulfate in a buffer containing 100 mM tris, 2.5 mM succinic acid, 10 mM EDTA and 500 mM LiCl at pH 6.5.
   6. Target rRNA Samples.
   rRNA samples were stored in water, 0.1% LiLS or Lysis Reagent prior to use in the experiments described herein.
B. Equipment and Material
   KingFisher® 96 (Thermo Electron, Waltham, Mass.)
   FLUOstar (BMG LABTECH, Germany)
   Eppendorf® Thermomixer R 022670565 (Eppendorf Corporation, Westbury, N.Y.)
   Hard-Shell Thin-Wall 96-Well Skirted PCR Plates, colored shell/white well, Catalog numbers: HSP-9615, HSP-9625, HSP-9635) (BioRad Hercules, Calif.)
   KingFisher® 96 tip comb for DW magnets (Catalog number: 97002534) Thermo Electron, Waltham, Mass.)
   DW 96 plate, V bottom, Polypropylene, sterile 25 pcs/case (Axygen Catalog number: P-2ML-SQ-C-S; VWR catalog number 47749-874)
   KingFisher® 96 KF plate (200 microliters) (Catalog number: 97002540)
   PTI® plate reader
   Chromo4™ plate reader
C. Target Capture
   Samples were mixed with Lysis Reagent to release target and stabilize rRNA. Target Capture Reagent was added. Ribosomal RNA target was captured and purified on magnetic particles using the KingFisher 96 purification system. Particles were resuspended in Amplification Reagent containing FAM-labeled Torch for analyte and TAMRA-labeled Torch for the internal control. A typical target capture procedure to purify and prepare nucleic acid samples for subsequent amplification was performed essentially as described below. 100 µL of test sample, 50 µL of the TCR containing target capture oligonucleotides, and 1 mL Lysis Reagent were combined and incubated at 60° C. for 15 minutes. The TCR magnetic particles from the treated reaction mixture were captured and washed using the Wash Solution and a suitable magnetic particle washing and separation device (e.g., a magnetic separation rack, a GEN-PROBE® Target Capture System, Gen-Probe Cat. No. 5207, or a KingFisher® magnetic particle processor system available from Thermo Labsystems). After washing, the magnetic particles were resuspended in 100 µL of the Amplification Reagent.

D. Amplification and Detection of Target

The real-time TMA amplification reactions were performed essentially as follows. 30 µL of sample, amplification and detection oligonucleotides in the Amp Reagent or 30 µL of the resuspended particles in the Amp Reagent from the target capture procedure was incubated at 60° C. for 10 minutes. The temperature was then reduced and the reaction mixture was equilibrated to 42° C. on an Eppendorf Thermomixer incubator for 15 minutes. 10 µL of Enzyme Reagent was added. The reaction mixture was mixed and incubated for 75 minutes at 42° C. in a real-time detection system (e.g., Opticon™ or Chromo4™ detection systems available from Bio-Rad Laboratories, or a PTI FluoDia® T70 instrument) for simultaneous amplification and detection of analyte and the internal control.

Example 2

Design and Initial Testing of *Salmonella* Oligonucleotide Sets

Using a region corresponding to the 350 region of the *E. coli* rRNA sequence, several T7 Providers, Blockers, Primers, and Torches were designed. This region was selected because it contains mismatches that are unique to other non-*Salmonella* enteric bacteria.

A total of 426 sets of T7, Blocker, Primer and Torch oligonucleotides were screened using a plate screening protocol. The SEQ ID NOs: of preferred oligonucleotides are given in Table 3. The number of oligonucleotides and concentrations used were: 8 different T7s (5 pmol/rxn); 7 different Blockers (0.5 pmol/rxn); 12 different Primers (5 pmol/rxn) and 5 different Torches (8 pmol/rxn). The target used was *Salmonella enterica* ssp. *enterica* sv. Enteritidis (ATCC 13076/GP60) rRNA at 1E+4 copies per rxn. The raw data collected were analyzed to calculate TTime values and RFU range. The data derived were grouped into sets giving TTime below 30 min, between 30 to 35 min, and those that were 35 to 39 min (Table 4).

TABLE 3

| Oligonucleotides Used for Screening 23S "350" Region | |
|---|---|
| Use | SEQ ID NOs: |
| T7 Providers | SEQ ID NOs: 1, 2, 3, 4, 5, 6, 7, 8 |
| Primers | SEQ ID NOs: 35, 36, 37, 38, 39, 40, 41, 42, 43, 44, 45, 46 |
| Torches | SEQ ID NOs: 66, 67, 68, 69, 70 |
| Blockers | SEQ ID NOs: 59, 60, 61, 62, 63, 64, 65 |

TABLE 4

RFU and TTime Values

Oligonucletide Combination

| SEQ ID Nos: of Provider: Blocker: Primer: Torch | RFU Range | TTime |
|---|---|---|
| SEQ ID NOs: 6: 64: 46: 66 | 33768 | 22.86 |
| SEQ ID NOs: 6: 64: 46: 68 | 14696 | 26.43 |
| SEQ ID NOs: 6: 64: 43: 66 | 26036 | 26.62 |
| SEQ ID NOs: 3: 61: 38: 70 | 19878 | 27.22 |
| SEQ ID NOs: 3: 61: 46: 70 | 25349 | 29.58 |
| SEQ ID NOs: 3: 61: 42: 66 | 27285 | 29.64 |
| SEQ ID NOs: 6: 64: 46: 69 | 10330 | 29.85 |
| SEQ ID NOs: 6: 64: 42: 66 | 29060 | 29.92 |
| SEQ ID NOs: 6: 64: 42: 67 | 26651 | 29.92 |
| SEQ ID NOs: 3: 61: 39: 68 | 19129 | 30.13 |
| SEQ ID NOs: 6: 64: 42: 68 | 18237 | 30.18 |
| SEQ ID NOs: 1: 59: 46: 68 | 8391 | 30.52 |
| SEQ ID NOs: 6: 64: 43: 68 | 18629 | 30.53 |
| SEQ ID NOs: 3: 61: 39: 66 | 27392 | 30.81 |
| SEQ ID NOs: 1: 59: 39: 66 | 26912 | 30.94 |
| SEQ ID NOs: 1: 59: 46: 66 | 25411 | 31.00 |
| SEQ ID NOs: 6: 64: 42: 70 | 33095 | 31.29 |
| SEQ ID NOs: 1: 59: 46: 67 | 25661 | 31.37 |
| SEQ ID NOs: 1: 59: 42: 67 | 34611 | 31.41 |
| SEQ ID NOs: 1: 59: 46: 70 | 16521 | 31.74 |
| SEQ ID NOs: 3: 61: 46: 68 | 22371 | 31.94 |
| SEQ ID NOs: 3: 61: 42: 70 | 24300 | 31.94 |
| SEQ ID NOs: 1: 59: 39: 68 | 13141 | 32.03 |
| SEQ ID NOs: 3: 61: 39: 70 | 19397 | 32.88 |
| SEQ ID NOs: 1: 59: 42: 68 | 12664 | 33.15 |
| SEQ ID NOs: 1: 59: 45: 70 | 16806 | 33.47 |
| SEQ ID NOs: 6: 64: 38: 66 | 18289 | 34.17 |
| SEQ ID NOs: 1: 59: 39: 70 | 18714 | 34.21 |
| SEQ ID NOs: 6: 64: 42: 69 | 9186 | 34.59 |
| SEQ ID NOs: 6: 64: 38: 68 | 18537 | 34.80 |
| SEQ ID NOs: 1: 59: 38: 68 | 17840 | 34.83 |
| SEQ ID NOs: 1: 59: 39: 67 | 18239 | 34.83 |
| SEQ ID NOs: 1: 59: 45: 67 | 30804 | 34.92 |
| SEQ ID NOs: 6: 64: 45: 68 | 18529 | 35.01 |
| SEQ ID NOs: 3: 61: 39: 67 | 21912 | 35.33 |
| SEQ ID NOs: 1: 59: 45: 68 | 9103 | 35.92 |
| SEQ ID NOs: 1: 59: 38: 70 | 18450 | 36.41 |
| SEQ ID NOs: 1: 59: 45: 66 | 13572 | 37.68 |
| SEQ ID NOs: 1: 59: 37: 69 | 13248 | 38.14 |
| SEQ ID NOs: 3: 61: 35: 68 | 20426 | 38.21 |
| SEQ ID NOs: 1: 59: 38: 67 | 15171 | 38.29 |
| SEQ ID NOs: 6: 64: 40: 68 | 18404 | 38.31 |
| SEQ ID NOs: 1: 59: 40: 70 | 11004 | 38.54 |
| SEQ ID NOs: 5: 63: 42: 66 | 26120 | 38.72 |
| SEQ ID NOs: 3: 61: 35: 67 | 17633 | 38.84 |
| SEQ ID NOs: 6: 64: 45: 70 | 27222 | 38.94 |
| SEQ ID NOs: 1: 59: 43: 67 | 16832 | 39.07 |
| SEQ ID NOs: 6: 64: 38: 67 | 18945 | 39.32 |
| SEQ ID NOs: 6: 64: 38: 70 | 15589 | 39.35 |

A secondary screening was performed on 42 potential oligonucleotide sets based on the initial screening. The oligonucleotides used are shown in Table 5.

TABLE 5

Oligonucleotides Used for Secondary Screening

| Use | SEQ ID NOs: |
|---|---|
| T7 Providers | SEQ ID NOs: 1, 3, 5, 6 |
| Primers | SEQ ID NOs: 35, 37, 38, 39, 40, 42, 43, 45, 46 |
| Torches | SEQ ID NOs: 66, 67, 68, 69, 70 |
| Blockers | SEQ ID NOs: 59, 61, 63, 64 |

In addition to repeating the reactivity to *S. Enteritidis* (GP60) rRNA, a preliminary cross-reactivity test against *E. coil* (GP88/ATCC10798) rRNA was also performed. From these results, 4 sets were identified that either did not cross-react with *E. coli* or did cross-react with *E. coli* but with a lag in the emergence time. These 4 oligonucleotide sets are shown in Table 6.

TABLE 6

Oligonucleotides Used for Additional Screening

| Oligonucleotide Set | Description | Oligonucleotide |
|---|---|---|
| Set #3 | T7 Provider | SEQ ID NO: 1 |
|  | Blocker | SEQ ID NO: 59 |
|  | Primer | SEQ ID NO: 39 |
|  | Torch | SEQ ID NO: 66 |
| Set #4 | T7 Provider | SEQ ID NO: 1 |
|  | Blocker | SEQ ID NO: 59 |
|  | Primer | SEQ ID NO: 43 |
|  | Torch | SEQ ID NO: 66 |
| Set #5 | T7 Provider | SEQ ID NO: 6 |
|  | Blocker | SEQ ID NO: 64 |
|  | Primer | SEQ ID NO: 45 |
|  | Torch | SEQ ID NO: 66 |
| Set #6 | T7 Provider | SEQ ID NO: 6 |
|  | Blocker | SEQ ID NO: 64 |
|  | Primer | SEQ ID NO: 42 |
|  | Torch | SEQ ID NO: 67 |

Initial specificity testing against other enteric bacteria (namely, *Enterobacter cloacae* and *Citrobacter freundii*) was performed for all 4 oligonucleotide sets. From these 4 oligonucleotide sets, the best oligonucleotide set was identified as Set #3 because it did not cross-react with *E. coli* (GP88), *E. cloacae* and *C. freundii*. It also did detect *Salmonella bongori*, the other species under the genus *Salmonella*. Repeat testing of *Salmonella* 23S oligonucleotide Set #3 was done with more replicates of *S. Enteritidis*, *S. bongori*, *C. freundii*, *E. cloacae* and 3 *E. coli* strains (GP3/ATCC25922, GP88/ATCC10798, and GP831/ATCC29214). *S. Enteritidis* and *S. bongori* rRNAs were again detected to a level similar to what was obtained previously. However, one *E. coli* strain (GP831) was also detected by this set of oligonucleotides.

Alternative Regions

Designs for the *Salmonella* genus project were started in the 450 region of the 16S rRNA (Table 7). Sequences were screened in that same manner as those in the 23S rRNA discussed above. Designs for the assay focused on the mismatches shown between bases 450-490. It was shown that the *Citrobacter* and *Enterobacter* strains were very close if not identical to the *Salmonella* in this region. It was also determined that *S. bongori* and *S. arizonae* were more similar to *E. coli* than other *Salmonella* and posed the risk of false negative generation. Initial screening results showed the inability of the 16S oligonucleotide system to discriminate the *Citrobacter* and *Enterobacter* strains tested. The data showed a very high false positivity rate that was inherent to the system. Based on initial screening results, it was decided to move forward with alternate designs (23S-350 region) since *Enterobacter* and *Citrobacter* could not be discriminated.

TABLE 7

Oligonucleotides Used for Screening 16S "450" Region

| Use | SEQ ID NO: | Sequence |
|---|---|---|
| Blocker | SEQ ID NO: 78 | gcggcauggcugcauccgga |
| Blocker | SEQ ID NO: 79 | cauacacgcggcaugcugc-X |
| Blocker | SEQ ID NO: 80 | uucauacacgcggcauggcu-X |
| Blocker | SEQ ID NO: 81 | ccuucuucauacacgcggca-X |
| Blocker | SEQ ID NO: 82 | cuucuucauacacgcg-X |
| Blocker | SEQ ID NO: 83 | gccuucuucauacacgcg-X |
| Blocker | SEQ ID NO: 84 | aggccuucuucauacacgcg-X |
| Blocker | SEQ ID NO: 85 | gaaggccuucuucauacacg |
| Blocker | SEQ ID NO: 86 | gaaggccuucuucauacacg-X |
| Blocker | SEQ ID NO: 87 | aacccgaaggccuucuuc-X |
| Blocker | SEQ ID NO: 88 | aguacuuuacaacccgaagg |
| Blocker | SEQ ID NO: 89 | cgcugaaaguacuuuacaac |
| T7 Provider | SEQ ID NO: 90 | ATTTAATACGACTCACTATAGGGAGAGCCGCGTGTATGAAGAAGGCCTTC-X |
| T7 Provider | SEQ ID NO: 91 | AATTTAATACGACTCACTATAGGGAGAGTGTATGAAGAAGGCCTTCGGGTTGTAAAG-X |
| T7 Provider | SEQ ID NO: 92 | ATTTAATACGACTCACTATAGGGAGAATGAAGAAGGCCTTCGGGTTGTAAAG-X |
| T7 Provider | SEQ ID NO: 93 | ATTTAATACGACTCACTATAGGGAGAGAAGGCCTTCGGGTTGTAAAG-X |
| T7 Provider | SEQ ID NO: 94 | ATTTAATACGACTCACTATAGGGAGACCACAAGAAGGCCTTCGGGTTGTAAAG-X |
| T7 Provider | SEQ ID NO: 95 | ATTTAATACGACTCACTATAGGGAGAGAAGGCCTTCGGGTGTAAAGTA-X |
| T7 Provider | SEQ ID NO: 96 | ATTTAATACGACTCACTATAGGGAGAGAAGGCCTTCGGGTGTAAAGTACTT-X |
| T7 Provider | SEQ ID NO: 97 | AATTTAATACGACTCACTATAGGGAGAGGCCTTCGGGTTGTAAAGTACTTTCAGCGG-X |
| T7 Provider | SEQ ID NO: 98 | ATTTAATACGACTCACTATAGGGAGACCTTCGGGTTGTAAAGTACTTTC-X |
| T7 Provider | SEQ ID NO: 99 | ATTTAATACGACTCACTATAGGGAGAGGGTTGTAAAGTACTTTCAGCGG-X |
| T7 Provider | SEQ ID NO: 100 | AATTTAATACGACTCACTATAGGGAGAGTTGTAAAGTACTTTCAGCGGGGAGGAAGG-X |
| T7 Provider | SEQ ID NO: 101 | ATTTAATACGACTCACTATAGGGAGAGTACTTTCAGCGGGGAGGAAGG-X |
| T7 Provider | SEQ ID NO: 102 | ATTTAATACGACTCACTATAGGGAGAGTACTTTCAGCGGGGAGGAAGG-X |
| T7 Provider | SEQ ID NO: 103 | ATTTAATACGACTCACTATAGGGAGAGTACTTTCAGCGGGGAGGAAGGGAGTAAAG-X |
| T7 Provider | SEQ ID NO: 104 | ATTTAATACGACTCACTATAGGGAGACAGCGGGGAGGAAGGGAGTAAAG-X |
| Extender | SEQ ID NO: 105 | TACTTTCAGCGGGGAGGAAGG |
| Extender | SEQ ID NO: 106 | TACTTTCAGCGGGGAGGAAGGGAG |
| Primer | SEQ ID NO: 107 | CGGGTTGTAAAGTACTTTCAGCGG |

TABLE 7-continued

Oligonucleotides Used for Screening 16S "450" Region

| Use | SEQ ID NO: | Sequence |
|---|---|---|
| Primer | SEQ ID NO: 108 | GAACCTAGTTGGGCGAGTTACGGAGTAACGTCAATTGCTGCGGT |
| Primer | SEQ ID NO: 109 | GTAACGTCAATTGCTGCGGT |
| Primer | SEQ ID NO: 110 | GGTAACGTCAATTGCTGCGG |
| Primer | SEQ ID NO: 111 | GAACCTAGTTGGGCGAGTTACGGAGGTAACGTCAATTGCTGCGG |
| Primer | SEQ ID NO: 112 | CTGCGGGTAACGTCAATTGCTG |
| Primer | SEQ ID NO: 113 | GAACCTAGTTGGGCGAGTTACGGACTGCGGGTAACGTCAATTGCTG |
| Primer | SEQ ID NO: 114 | GTTTGTATGTCTGTTGCTATTATGTCTACCTTCTTCTGCGGGTAACGTCAATG |
| Primer | SEQ ID NO: 115 | cacgGAGTTAGCCGGTGCTTC |
| Primer | SEQ ID NO: 116 | cugcTGGCACGGAGTTAGCCGGTGCTTC |
| Primer | SEQ ID NO: 117 | GTTTGTATGTCTGTTGCTATTATGTCTACCTGCTGGCACGGAGTTAGCCGGTGCTTC |
| Primer | SEQ ID NO: 118 | GTCTACGCGGCTGCTGGCACGGAGTTAGCCGGTGCTTC |
| Primer | SEQ ID NO: 119 | GAACCTAGTTGGGCGAGTTACGGAGTCTACGCGGCTGCTGGCACGGAGTTAGCCGGTGCTTC |
| Primer | SEQ ID NO: 120 | cugcTGGCACGGAGTTAGC |
| Primer | SEQ ID NO: 121 | cgcuTGCACCCTCCGTATTACCGCGGC |
| Primer | SEQ ID NO: 122 | cgcuTGCACCCTCCGTATTACC |
| Primer | SEQ ID NO: 123 | GTTTGTATGTCTGTTGCTATTATGTCTACGGAUTTCACATCTGACTTAACAAAC |
| Torch | SEQ ID NO: 124 | ggggcuuuacucccuuccuccc |
| Torch | SEQ ID NO: 125 | ggagg9accacaacaccuuccucc |
| Torch | SEQ ID NO: 126 | ggagg9uuauuaaccacaacaccuuccucc |
| Torch | SEQ ID NO: 127 | cgagg9accacaacaccuuccucg |
| Torch | SEQ ID NO: 128 | ccaacuuuacucccuuccucguugg |
| Torch | SEQ ID NO: 129 | gcaaagguauuaacuuuacucccuuccuuugc |
| Torch | SEQ ID NO: 130 | ggaagg9uuauuaaccacaacaccuucc |
| Torch | SEQ ID NO: 131 | gcaaagguauuaacuuuacucccuuugc |
| Torch | SEQ ID NO: 132 | gggaggguauuaacuuuacuccc |
| Torch | SEQ ID NO: 133 | cggug9uuauuaaccacaacaccg |
| Torch | SEQ ID NO: 134 | gguguu9auuaaccacaacacc |
| Torch | SEQ ID NO: 135 | cggug9gcugcgguuauuaaccacaacaccg |
| Torch | SEQ ID NO: 136 | cgcugcgguuauuaaccacaa9cagcg |
| Torch | SEQ ID NO: 137 | gcugcgguuauuaaccacaaca9gcagc |
| Torch | SEQ ID NO: 138 | ccugcugcgguuauuaaccacaaca9gcagg |
| Torch | SEQ ID NO: 139 | ccgaggagcaaagguauuaacuuuacucgg |
| Torch | SEQ ID NO: 140 | cgagcaaagguauuaacuuuacucgcucg |
| Torch | SEQ ID NO: 141 | cgagcaaagguauuaacuuuacugcucg |

TABLE 7-continued

Oligonucleotides Used for Screening 16S "450" Region

| Use | SEQ ID NO: | Sequence |
|---|---|---|
| Torch | SEQ ID NO: 142 | cgagcaaagguauuaacuuuacgcucg |
| Torch | SEQ ID NO: 143 | cgagcaaagguauuaacuuuagcucg |
| Torch | SEQ ID NO: 144 | cgagcaaagguauuaacuuugcucg |
| Torch | SEQ ID NO: 145 | cgagcaaagguauuaacgcucg |
| Torch | SEQ ID NO: 146 | ccgucaaugagcaaaggacgg |
| Torch | SEQ ID NO: 147 | cggguaacgucaaugagcaaaggacccg |
| Torch | SEQ ID NO: 148 | cugcggguaacgucaaugagcaaacgcag |
| Torch | SEQ ID NO: 149 | ccugcggguaacgucaaugagcagg |

Lower case 2'-O--methyl RNA
X is a blocking moiety (e.g., reverse(3'-5') C blocked)
9 is a non-nucleotide (triethylene glycol) linker joining region, and 5'-fluorescein ("F") fluorophore and 3'-dabsyl ("D") quencher moieties were attached to the torch oligonucleotides Accordingly, the 350 region of the 23S rRNA was selected as the preferred region for further optimization based upon the finding that T7 providers and primer oligonucleotides for this region displayed the highest signals and lowest background in a single primer TMA assay, relative to the large number of other oligonucleotide sets tested. Screening of oligonucleotides in a TMA assay was performed, and different Torches and Blockers were also analyzed. The criteria for selecting the best oligonucleotide sets included having the lowest background and the highest signal at 1 E+5 copies of *Salmonella* rRNA.

Example 3

Further Identification of *Salmonella* Oligonucleotide Sets

To further reduce background signals and improve specificity and sensitivity, a number of additional oligonucleotide sets were designed and tested.

Based on oligonucleotide set #3 several redesigned T7 providers and primer oligonucleotides were identified that took advantage of mismatches found in *E. coli*. Real-time TMA was run on the redesigned 23S T7 providers and primer oligonucleotides. The number of oligonucleotides and concentrations used were: 10 different T7 Providers (5 pmol/reaction); 1 Blocker (0.5 pmol/reaction); 6 Primer oligonucleotides (5 pmol/reaction) and 1 Torch oligonucleotide (8 pmol/reaction). The identities of the oligonucleotides are shown in Table 8.

TABLE 8

Redesigned Oligonucleotides

| Use | SEQ ID NO: |
|---|---|
| T7 Providers | SEQ ID NOs: 1, 10, 11, 12, 13, 14, 15, 16, 17, 18 |
| Primers | SEQ ID NOs: 39, 40, 43, 47, 48, 49 |
| Blocker | SEQ ID NO: 59 |
| Torch | SEQ ID NO: 66 |

The targets used were *S. Enteritidis* GP60 rRNA at 1E+4 copies per reaction, *S. bongori* at 1E+4 copies per reaction, *E. coli* GP88 rRNA at 1E+6 copies/rxn and *E. coli* GP831 rRNA at 1E+6 copies/rxn. A total of 60 sets were tested and 10 potential oligonucleotide sets from this redesigned set were identified to give respectable TTimes and RFU ranges for *S. Enteritidis*, but some did not react with *S. bongori* or did cross-react with *E. coli* GP88 and/or *E. coli* GP831 (Table 9).

TABLE 9

TTime and RFU range of 10 Potential Oligonucleotide Sets

| OLIGO COMBINATION Provider: Blocker: Primer: Torch (SEQ ID NOs:) | Target > | SE at $10^4$ | SB at $10^4$ | EC0088 at $10^6$ | EC0831 at $10^6$ |
|---|---|---|---|---|---|
| SEQ ID NOs: 1: 59: 39: 66 | TTIME | 29.49 | 30.16 | 0 | 37.44 |
|  | RFU | 34.713 | 1.113 | 0 | 22.417 |
| SEQ ID NOs: 12: 59: 47: 66 | TIME | 34.11 | 40.06 | 0 | 40.19 |
|  | RFU | 30.963 | 3.357 | 0 | 14.759 |
| SEQ ID NOs: 12: 59: 49: 66 | TTIME | 28.67 | 30.53 | 30.91* | 34.19 |
|  | RFU | 32.554 | 15.103 | 1145* | 26.336 |
| SEQ ID NOs: 13: 59: 47: 66 | TTIME | 32.17 | 44.14 | 0 | 40.37 |
|  | RFU | 29.643 | 3.037 | 0 | 2.541 |
| SEQ ID NOs: 13: 59: 48: 66 | TTIME | 28.42 | 38.55 | 44.91 | 36.4 |
|  | RFU | 28.184 | 11.519 | 1.534 | 4.687 |
| SEQ ID NOs: 14: 59: 49: 66 | TTIME | 27.5 | 33.24 | 0 | 39.29 |
|  | RFU | 27.505 | 14.480 | 0 | 18.138 |

TABLE 9-continued

TTime and RFU range of 10 Potential Oligonucleotide Sets

OLIGO COMBINATION
Provider: Blocker:

| Primer: Torch (SEQ ID NOs:) | Target > | SE at 10^4 | SB at 10^4 | EC0088 at 10^6 | EC0831 at 10^6 |
|---|---|---|---|---|---|
| SEQ ID NOs: 15: 59: 49: 66 | TTIME | 30.83 | 32.22 | 43.11 | 46.27 |
|  | RFU | 35.564 | 1.766 | 1.014 | 19.568 |
| SEQ ID NOs: 17: 59: 48: 66 | TTIME | 33.96 | 34.24 | 46.01** | 44.58 |
|  | RFU | 22.283 | 1.854 | 2018** | 19.210 |
| SEQ ID NOs: 17: 59: 49: 66 | TTIME | 30.46 | 30.7 | 46.12 | 42.08 |
|  | RFU | 27.194 | 25.054 | 21.684 | 14.927 |
| SEQ ID NOs: 10: 59: 48: 66 | TTIME | 35.56 | 43.06 | 52.25 | 45.31 |
|  | RFU | 29.914 | 20.081 | 1.327 | 10.999 |

*0 target had lower TTime and same RFU;
**0 target had higher Ttime and lower RFU Lower TTime and higher TTime refer to earlier and later emergence of signal, respectively.

Real-time TMA was used to screen a subset of the above 10 sets using the following concentrations: T7 Providers at 5 pmol/reaction; Blocker oligonucleotide at 0.5 pmol/rxn; Primer oligonucleotides at 5 pmol/reaction and Torch oligonucleotide at 8 pmol/rxn. The targets used were *S. Enteritidis* rRNA at 1 E+4 cps/rxn, *S. bongori* at 1 E+4 cps/rxn; 13 strains of *E. coli* at 1E+7 cps/rxn, *S. bongori* at 1E+4 cps/rxn; *C. freundii* at 1E+6 cps/rxn; *E. cloacae* at 1E+6 cps/rxn; 2 strains of *Shigella flexneri* at 1E+6 cps/rxn, and *Shigella sonnei* at 1E+6 cps/rxn.

The T7 Provider and primer oligonucleotides were mixed and matched to provide 4 possible sets to test that are shown in Table 10.

TABLE 10

Oligonucleotide Sets

| Oligonucleotide Set | Description | Oligonucleotide |
|---|---|---|
| Set 3 | T7 Provider | SEQ ID NO: 1 |
|  | Blocker | SEQ ID NO: 59 |
|  | Primer | SEQ ID NO: 39 |
|  | Torch | SEQ ID NO: 66 |
| Set 7 | T7 Provider | SEQ ID NO: 1 |
|  | Blocker | SEQ ID NO: 59 |
|  | Primer | SEQ ID NO: 49 |
|  | Torch | SEQ ID NO: 66 |
| Set 8 | T7 Provider | SEQ ID NO: 17 |
|  | Blocker | SEQ ID NO: 59 |
|  | Primer | SEQ ID NO: 39 |
|  | Torch | SEQ ID NO: 66 |
| Set 9 | T7 Provider | SEQ ID NO: 17 |
|  | Blocker | SEQ ID NO: 59 |
|  | Primer | SEQ ID NO: 49 |
|  | Torch | SEQ ID NO: 66 |

These sets were tested against all 13 strains of *E. coli* (ATCC#'s 25922, 11775, 10798, 35150, 33780, 23722, 25404, 29214, 29194, 35359, 23499, 12792, and 23503), then against other enteric bacteria. The TTime and RFU results were compared to each other. Using the best 3 oligonucleotide sets obtained from the *E. coli* results, real-time TMA was run on several other enteric bacteria using sets #3, #7, and #9. All 3 oligonucleotide sets picked up *S. enterica* with TTimes of 28 min, 25 and 23 min, respectively. *S. bongori* was also picked up by these 3 oligonucleotide sets with TTimes of 32 min, 30 min and 26 min, respectively. Some other enteric bacteria showed some cross-reactivity, but had very late emergence times and low RFU levels.

Based on the results obtained, further assay testing and optimization focused on 2 oligonucleotide sets: #7 and #9 (Table 10). Sensitivity of detecting various copy levels of *S. Enteritidis* GP60 rRNAs in a pure system (no target capture step) using oligonucleotide sets #7 and #9 was tested. At 1E+5 copies, TTime was in the low 20 min range for both sets of oligonucleotides. Oligonucleotide set #7 detected 83% of replicates at the 100-copy level. Oligonucleotide set #9 detected 100% of replicates at the 50-copy level.

Example 4

Further Characterization and Optimization of *Salmonella* Oligonucleotide Sets

Based on the results of set #7 showing better specificity than set #9 and of set #9 showing better sensitivity than set #7, new oligonucleotide redesigns of both T7 provider and primer oligonucleotides were prepared.

Oligonucleotide Set #7

Newly redesigned T7 oligonucleotide providers were tested and compared to the original T7 Provider sequence of SEQ ID NO: 1, which, in combination with the Blocker sequence of SEQ ID NO: 59, the primer sequence of SEQ ID NO: 49, and the Torch sequence of SEQ ID NO: 66, provided the least cross-reactivity to *E. coli*. Amplification performance was evaluated for each set of oligonucleotides compared to set #7. The targets all went through Target Capture step using the sequence of SEQ ID NO: 74. From the data and shape of the curves, T7 provider sequences of SEQ ID NOs: 24 and 26 were selected to be further evaluated.

Oligonucleotide Set #9

Primer oligonucleotides of SEQ ID NOs: 50 and 51 were redesigned from the sequence of SEQ ID NO: 49 to take advantage of other possible mismatches to *E. coli* and in order to reduce cross-reactivity of the sequence of SEQ ID NO: 49 to *E. coli*. Testing was done without target capture to establish baseline performance measurement.

Table 11 presents redesigned oligonucleotides. The redesigned oligonucleotides had the lowest relative fluorescence unit (RFU) and the longest TTime at the zero rRNA copy level. High RFU values at the zero rRNA copy level indicated possible contamination within the reagents.

TABLE 11

Redesigned Oligonucleotides

| Use | SEQ ID NO: |
|---|---|
| T7 Provider | SEQ ID NOs: 19, 20, 21, 22, 23, 24, 25, 26 |
| Primer | SEQ ID NOs: 50, 51 |

Based on the results obtained, it was determined that the oligonucleotide set #1 had a better specificity than set #9. This oligonucleotide set had less cross-reactivity to *E. coli* and was used as one of the oligonucleotide systems for further study.

The other oligonucleotide set used for further study was set #2. The structural basis for choosing these two oligonucleotide sets was based on the combination of enough mismatches to discriminate *Salmonella* from other enteric bacteria and enough matches to detect all *Salmonella* subspecies. This would allow the amplification system to achieve the required specificity and sensitivity. The two preferred oligonucleotide sets are shown in Table 2.

Confirmatory testing was performed on both oligonucleotide sets. For set #1, using the new concentrations of T7 (15 pmol), primer (15 pmol) and Blocker (5 pmol) for analyte, and T7 (2 pmol) and primer (2 pmol) for IC, there was a significant improvement in both TTimes (at least 10-15 min earlier at 1E+5-1E+4 *S. Enteritidis* target copies) and curve shape (standing up and tight). For set #2, using the new concentrations of T7 (15 pmol) and primer (15 pmol) for analyte, and T7 (2 pmol) and primer (2 pmol) for IC, there was a significant improvement in both TTimes (at least 10-17 min earlier at 1E+5-1E+4 *S. Enteritidis* target copies) and curve shape (standing up and tight).

Example 5

Evaluation of Target Capture Integration and Internal Control (IC) Integration

Seven *Salmonella* 23S target capture oligonucleotides (SEQ ID NOs: 71-77 were tested using two sets of amplification oligonucleotides: set #7 and set #9. The target capture procedure was performed on varying amounts of *S. Enteritidis* GP60 rRNAs and against 1E+7 copies of *E. coli* GP88 rRNAs. Two potential useful target capture oligonucleotide (TCO) sequences were identified (SEQ ID NOs: 71 and 74). Overall, the TTime observed was about 8 to 10 min later than in a pure system. Target capture oligonucleotide of SEQ ID NO: 74 was chosen for use in all subsequent experiments.

The method of Target Capture with Kingfisher 96 is summarized in Table 12. Amplification and Enzyme reagents were reconstituted. A wash plate was prepared by filling a KF200 plate with 200 μL/well of wash solution. An amp plate was prepared by filling another KF200 plate with 100 μL/well of amplification reagent. Both the amp and wash plates were covered until used. A sample plate was prepared by adding 50 μL TCR/well into a 2-mL, deep-well 96 plate (Axygen). The target was diluted to the required concentrations in 10 μL, lysis solution. One ml of lysis solution was added to each well of the sample plate. With a repeat pipettor, 10 μL of target solution was added to the appropriate deep wells. A deep-well tip-comb was placed in the sample plate. The covers for the wash and amp plates were removed. The KF96 protocol was started and all three plates were placed on the KF96 instrument. The amp plate was placed in position 4, the wash plate in position 3, and the sample (deep-well plate) in position 1. Position 2 in the KF96 instrument was left empty. Once the plates were loaded, the KF96 instrument began the target capture step. When the KF96 run was completed, the plates were removed. From the amp plate, 30 μL from each well were removed using a multi-channel pipettor and transferred to an MJ 96-well PCR plate.

TABLE 12

Kingfisher 96 Program

| Step | Position | Step Description | Action | Beginning | Mix | End |
|---|---|---|---|---|---|---|
| 1 | 1 | Capture | Heat | 5 min-85° C. | Very slow | No action |
| 2 | 1 | Capture | Heat | 15 min-65° C. | Very slow | No action |
| 3 | 2 | Cool | Heat | 30 min-25° C. (table rotated to empty position) | No action | No action |
| 4 | 1 | Mix prior to collect/collect Sample 1 | Mix | No action | 1 min-Very slow | Collect beads-count 20 |
| 5 | 3 | Release to Wash | Wash | Release 30 s Slow | 30 s Slow | No action |
| 6 | 1 | Capture Sample 2 | Wash | Release 30 s Very Slow (mix only) | 30 s Very Slow | Collect beads-count 20 |
| 7 | 3 | Release to Wash 2 | Wash | Release 30 s Slow | 30 s Slow | Collect beads-count 20 |
| 8 | 4 | Capture and release into Amp Soln | Wash | Release 30 s Slow | 30 s Slow | No action |

An Internal Control (IC) was integrated into the *Salmonella* prototype assay with target capture. This set of IC oligonucleotides performed well for the *Salmonella* system with average TTimes in the 19-20 min range and curves that were tight, sharp and standing up. With the IC integration, the sensitivity of the *Salmonella* assay dropped by about 10-fold, although it did not seem to affect specificity to other enteric bacteria.

TABLE 13

Oligonucleotide Components used for the Complete System using Oligonucleotide Set #2 with IC system

| Component | *Salmonella* |
|---|---|
| T7 Provider | SEQ ID NO: 26 at 5 pmol |
| Blocker | SEQ ID NO: 59 at 0.5 pmol |
| Primer | SEQ ID NO: 49 at 10 pmol |
| Torch | SEQ ID NO: 66 at 8 pmol |
| Target Capture | SEQ ID NO: 74 at 5 pmol |
| Target reference | *S. Enteritidis* GP60 rRNA |

Example 6

Sensitivity, Specificity, Interference, Limit of Detection, Cross-Reactivity, and Time to Results Stage I Sensitivity

*Salmonella* Enteritidis, ATCC 13076, was assayed at 1E+5 copies/reaction. Lysis buffer was used as the negative control. Twenty positives ($10^5$ copies of rRNA/assay) were tested using the KingFisher 96 instrument for target capture and the PTI reader for detection. Twenty negatives (lysis buffer) were used as control. The input for target capture was 1 mL, the output for target capture was 100 µL of which 30 µL was used in the amplification. The positive criterion was 1,000 RFU. Nineteen of 20 replicates were to be detected with >95% positivity rate. If less than 19 replicates were positive after an initial round of testing, 40 additional replicates were to be tested. Testing for Stage I-Sensitivity yielded a 100% rate of positivity for *Salmonella* Enteritidis at 1 E+5 copies/reaction and 0% false positivity at 0 copies.

Specificity

Organisms that were closely related to the target organism but were genotypically distinct by rRNA analysis were chosen as negatives. Eight challenge organisms were tested at 1 E+7 copies/rxn using the Kingfisher96 instrument for target capture, the Eppendorf thermomixer for annealing of primers and enzyme addition, and the PTI reader for detection. Twenty reactions of all challenge organisms (8) were tested with one replicate of each reaction amplified ($10^5$ copies of rRNA, ~100 CFU/assay). *S. Enteritidis*, ATCC 13076, was used as a positive control at 1E+5 copies/rxn and lysis solution used as a negative control. The positive criterion was 1,000 RFU. Less than or equal to 8 of 160 reactions were to meet the goal (to discriminate and not detect $10^5$ copies of non-target rRNA) of ≤5% combined false positivity rate. The dispersion of any false positives across the 8 organisms was to be considered. Organisms with clustered false positivity ≥4 were to be retested and investigated further. Stage I-Specificity testing showed 0% positivity against any of the challenge organisms tested and 100% positivity with the positive control.

Interference

The goal was repeatable detection of rRNA approximately equivalent to 10-100 CFUs rRNA spiked into a volume of lysis buffer expected to be obtained from the sample concentration device. Testing was to include low copy numbers of desired rRNA and $10^7$ copies rRNA (~10,000 CFU) nearest neighbor organisms. *S. Enteritidis*, ATCC 13076, was used as the baseline target and was tested at 1 E+5 copies rRNA/reaction (approximately 100 CFUs). Eight challenge organisms were spiked into the samples at a concentration of 0 (lysis solution only) or 1E+7 copies (approximately 10,000 CFU). Assays were performed using the Kingfisher 96 and the PTI reader. All conditions were tested in replicates of 12 with a positive criterion of 1,000 RFU. Results were to report the reproducibility of positivity in the presence of the nearest neighbor organisms. The dispersion of interference across the organisms tested was to be considered. Organisms exhibiting interference were to be retested and investigated further. Stage I-Interference testing showed 100% positivity in all challenge samples and positive controls.

Microbial Flora Determination

Twenty poultry rinses were analyzed at Gen-Probe to provide an estimate of the normal flora associated with poultry rinse. Eighteen of 20 rinses were part of one batch that was received from a source outside of Gen-Probe. The other two samples were derived at Gen-Probe from chickens purchased at 2 local grocery stores. Dilution plating for total aerobic count on TSA plates was conducted. Dilutions of 1E+1 through 1E+4 of each poultry rinsate sample were prepared in 1X phosphate buffered saline. 100 µL of undiluted, 1E+1 through 1E+4 rinsate dilutions were plated on tryptic soy agar (TSA) plates.

Colony counts were performed after the plates had been incubated at 30° C. and 35-37° C. for 24-48 hours. Colonies representing different morphologies were sent to PACE Analytical Life Sciences (Minneapolis, Minn.) for identification by RiboPrinter® microbial characterization system. In addition to TSA counts and riboprinting, samples were enriched in buffered peptone water (BPW) followed by selective enrichment with either TT broth or mRSV broth (semi-solid). Samples from the selective enrichment were plated on both BGS and XLT4 agar plates for further selectivity. BIOLOG identification and Gram stain/oxidase testing were performed on representative colonies. Results showed normal flora in the poultry rinse.

For *Salmonella* selection, 90 ml buffered-peptone water (BPW) was inoculated with 10 ml of poultry rinsate and enriched at 35° C. for 24 hours. Ten ml of mRSV (modified Rappaport-Vassiliadis-Bouillion) broth was inoculated with 100 µL of enriched sample and incubated at 42° C., shaking, for 24 hours. Ten ml of TT broth (Hajna) was inoculated with 500 µL of enriched sample and incubated at 42° C., shaking, for 24 hours. Ten µL samples from both selective media (mRSV and TT) were plated on both XLT4 (xylose lysine tetrathionate) and BGS (brilliant green selenite) agar plates. The inoculated plates were incubated at 35° C. and examined at 24 and 48 hours. Selected colonies from the XLT4 and BGS plates were plated on opposite media. For example, if a colony was chosen from the XLT4 plate, it was plated on BGS media, and visa versa. Selected colonies were plated on TSA, from which BIOLOG identification and Gram stain/oxidase testing were performed to confirm the identification of the microorganism.

Glycerol stocks of selected colonies were made and sent to PACE Analytical for riboprinting for confirmation of microorganism identity.

Stage II

Stage II performance testing evaluated the preliminary amplification assay in Buffered-Peptone Water (BPW). The evaluation used pure culture lysates. Sample preparation device was not included. All positive controls (at 1 E+5 copies/assay) used the purified RNA isolated from *S. enterica* ssp. *enterica* sv. Enteritidis ATCC 13076 and negative control was lysis solution:BPW (7:3). Three hundred µL BPW and 700 µL lysis buffer (with or without sample) were used to make a 1 mL input for target capture. The input for target capture was 1 mL, the output for target capture was 100 µL of which 30 µL was used in the amplification.

Sensitivity

*S. enterica* ssp. *enterica* sv. Choleraesuis (ATCC 10708), *S. enterica* ssp. *enterica* sv. Typhi (ATCC 19430) and *S. enterica* ssp. *enterica* sv. Typhimurium (ATCC 13311) were tested at a level of 1E4-5E4 copies RNA/assay (approximately 10-50 CFU). All three species and negative control (unspiked BPW) were tested in replicates of 20. Target capture was performed on the Kingfisher 96 instrument, with enzyme addition on the Eppendorf thermomixer, followed by detection on the PTI reader. The positive criterion parameter for the sensitivity was 1,000 RFU. Nineteen of the 20 replicates were to be positive. If less than 19 of 20 were positive, further testing of an additional 40 replicates was required. All organisms tested for sensitivity passed the Stage II requirement.

Limit of Detection

The goal was repeatable detection of $10^3$-$10^4$ equivalent copies rRNA (~1-10 CFU) per assay input volume. Repeatable detection was defined as ≥95% positivity. *S. enterica* ssp. *enterica* sv. Choleraesuis (ATCC 10708), *S. enterica* ssp. *enterica* sv. Typhi (ATCC 19430), *S. enterica* ssp. *enterica* sv. Typhimurium (ATCC 13311), *S. enterica* ssp. *enterica* sv. Enteritidis (ATCC 13076), *S. enterica* ssp. *enterica* sv. Gallinarum (ATCC 9184) and *S. enterica* ssp. *arizonae* (ATCC 29933) were tested at a level of 1E3-1E4 copies RNA/assay (approximately 1-10 CFU). Target capture was performed on the Kingfisher 96, enzyme addition on the Eppendorf thermomixer, and the detection on the PTI reader. Each species was tested in replicates of 20. The lysates were prepared from pure culture target organisms quantitated in CFUs and lysed to provide nucleic acid target at a level equivalent to ~1-10 CFU. The positive criterion was 1,000 RFU. *S. Enteritidis*, ATCC 13076, was considered both the positive control as well as a strain required for testing. For LOD testing, the Positive Control RNA was used at 1E+4 copies/assay. The criteria was ≥95% positivity for all of the species tested. If less than 19 of 20 were positive, further testing of an additional 40 replicates was required. All organisms passed the Stage II requirement.

Analytical Testing of Inclusive and Exclusive Species

Twenty-two Inclusive organisms and twenty-two Exclusive organisms were tested at 1E+5 copies/assay (approximately 100 CFU). Testing was performed on the Kingfisher 96 instrument for target capture, enzyme addition on the Eppendorf thermomixer, and the PTI reader for detection. All were tested in replicates of 4 for the Inclusives and replicates of 8 for the Exclusives.

For the Inclusives, 3 of 4 replicates were to be positive and, for the Exclusives, no more than 1 of 8 replicates were to be positive. If these criteria were not met for any organism, testing for that species/strain was repeated in replicates of 12, where 11 of 12 replicates of Inclusives were to be reactive. The identity of organisms that failed the inclusivity criterion after retest were to be further investigated. For Exclusives that did not meet retesting criterion [<3/12 positive], cross-reacting organisms were further investigated.

TABLE 14

Positivity Rate for Inclusives Testing

| Organism | Serovar | ATCC # | Copies per Reaction | No. of Reactions | No. of Replicates | Positives | Positivity |
|---|---|---|---|---|---|---|---|
| *S. enterica* ssp. *enterica* | Typhimurium | 33062 | 1E5 | 4 | 1 | 4 | 100% |
| *S. bongori* | | 43975 | 1E5 | 4 | 1 | 0 | 0% |
| *S. enterica* ssp. *enterica* | Harmelen | 15783 | 1E5 | 4 | 1 | 4 | 100% |
| *S. enterica* ssp. *enterica* | Heidelberg | 8326 | 1E5 | 4 | 1 | 4 | 100% |
| *S. enterica* ssp. *enterica* | Newport | 6962 | 1E5 | 4 | 1 | 4 | 100% |
| *S. enterica* ssp. *enterica* | Muenchen | 8388 | 1E5 | 4 | 1 | 4 | 100% |
| *S. enterica* ssp. *enterica* | Typhi | 6539 | 1E5 | 4 | 1 | 4 | 100% |
| *S. enterica* ssp. *enterica* | Saint Paul | 9712 | 1E5 | 4 | 1 | 4 | 100% |
| *S. enterica* ssp. *enterica* | Montevideo | 8387 | 1E5 | 4 | 1 | 4 | 100% |
| *S. enterica* ssp. *enterica* | Paratyphi A | 9150 | 1E5 | 4 | 1 | 4 | 100% |
| *S. enterica* ssp. *enterica* | Paratyphi B | 10719 | 1E5 | 4 | 1 | 4 | 100% |
| *S. enterica* ssp. *enterica* | Paratyphi C | 13428 | 1E5 | 4 | 1 | 4 | 100% |
| *S. enterica* ssp. *arizonae* | | 33952 | 1E5 | 4 | 1 | 4 | 100% |
| *S. enterica* ssp. *diarizonae* | | 29934 | 1E5 | 4 | 1 | 4 | 100% |
| *S. enterica* ssp. *enterica* | Typhimurium | 14028 | 1E5 | 4 | 1 | 4 | 100% |
| *S. enterica* ssp. *enterica* | Illinois | 11646 | 1E5 | 4 | 1 | 4 | 100% |
| *S. enterica* ssp. *enterica* | Hooggraven | 15786 | 1E5 | 4 | 1 | 4 | 100% |
| *S. enterica* ssp. *enterica* | Cubana | 12007 | 1E5 | 4 | 1 | 0 | 0% |
| *S. enterica* ssp. *enterica* | Rubislaw | 10717 | 1E5 | 4 | 1 | 4 | 100% |
| *S. enterica* ssp. *enterica* | Panama | 7378 | 1E5 | 4 | 1 | 4 | 100% |
| *S. enterica* ssp. *enterica* | Gallinarum | 9184 | 1E5 | 4 | 1 | 4 | 100% |
| *S. enterica* ssp. *indica* | Ferlac | 43976 | 1E5 | 4 | 1 | 4 | 100% |

TABLE 14-continued

Positivity Rate for Inclusives Testing

| Organism | Serovar | ATCC # | Copies per Reaction | No. of Reactions | No. of Replicates | Positives | Positivity |
|---|---|---|---|---|---|---|---|
| Positive* | | 13076 | 1E5 | 12 | 1 | 12 | 100% |
| Negative* | | NA | 0 | 12 | 1 | 0 | 0% |
| Repeat Testing | | | | | | | |
| S. bongori | | 43975 | 1E5 | 12 | 1 | 0 | 0% |
| S. enterica ssp. enterica | Cubana | 12007 | 1E5 | 12 | 1 | 12 | 100% |

*Total for all runs

TABLE 15

Positivity Rate for Exclusives Testing

| Organism | ATCC#/ other | Copies per Reaction | Number of Reactions | Number of Replicates | Positives | Positivity |
|---|---|---|---|---|---|---|
| E. coli | 25922 | 1E5 | 8 | 1 | 0 | 0% |
| E. vulneris | 33833 | 1E5 | 8 | 1 | 0 | 0% |
| E. hermannii | 55236 | 1E5 | 8 | 1 | 0 | 0% |
| E. cloacae | 700644 | 1E5 | 8 | 1 | 0 | 0% |
| E. aerogenes | 13048 | 1E5 | 8 | 1 | 0 | 0% |
| E. hoshinae | 33379 | 1E5 | 8 | 1 | 0 | 0% |
| P. mirabilis | 29906 | 1E5 | 8 | 1 | 0 | 0% |
| C. brakii | 29063 | 1E5 | 8 | 1 | 0 | 0% |
| P. fluorescens | 13525 | 1E5 | 8 | 1 | 0 | 0% |
| S. flexneri | 12022 | 1E5 | 8 | 1 | 0 | 0% |
| C. freundii | 33128 | 1E5 | 8 | 1 | 0 | 0% |
| C. koseri/diversus | CI495 | 1E5 | 8 | 1 | 0 | 0% |
| K. pneumoniae | 23357 | 1E5 | 8 | 1 | 0 | 0% |
| S. marcescens | 13880 | 1E5 | 8 | 1 | 0 | 0% |
| L. innocua | 33090 | 1E5 | 8 | 1 | 0 | 0% |
| E. faecalis | 33186 | 1E5 | 8 | 1 | 0 | 0% |
| C. jejuni | 33560 | 1E5 | 8 | 1 | 0 | 0% |
| C. coli | 43478 | 1E5 | 8 | 1 | 0 | 0% |
| S. pneumoniae | 6303 | 1E5 | 8 | 1 | 0 | 0% |
| Positive* | 13076 | 1E5 | 8 | 1 | 8 | 100% |
| Negative* | NA | 0 | 8 | 1 | 0 | 0% |

*Total for all runs

Testing for the Stage II—Analytical Testing of Inclusives (Table 14) and Exclusives (Table 15) was considered complete except for the single minor exception of *Salmonella bongori* inclusivity. *S. bongori* was not detected upon initial testing of 4 replicates (0 pos/4 reps) and retesting of 12 replicates (0 pos/12 reps) (Table 14). For *S. bongori*, retesting was done on a new lysate tube from the current lot of *S. bongori* ATCC 43975 after determination of RNA concentration using Gen-Probe's MTC-NI (cat. no. 4573). Testing was also performed on other strains of *S. bongori*, but none was amplified by the current *Salmonella* assay. Due to the rare isolation of this organism, detection of *S. bongori* was not considered a requirement for the assay as *S. bongori* has only been isolated twice out of 36,184 isolates and is not in the top 30 isolates per the CDC 2005 *Salmonella* Annual Summary. For *S. Cubana* retesting, a new lysate tube was used from the same lot used in the initial testing. Upon retesting, *S. Cubana* (12 pos/12 reps) passed Stage 2 acceptable criteria for retesting.

Time-to-Result

The time of each assay run for Stage II was tracked from the time samples were added to the deep-well plate through the end of the PTI reader protocol. The average time from sample loading to the start of the PTI reader was 2 hours, 18 minutes for 96 samples. The PTI reader time was static at 75 minutes. Therefore, the whole assay from start to finish was 3 hours, 33 minutes on average for 96 samples.

These results indicate that the species-specific detection of *Salmonella* can be achieved by the compositions and methods even in the presence of closely related organisms, based upon the characteristics of the real-time TMA data (e.g., the size and shape of RFU curves generated from the real-time TMA reactions).

Example 7

Food Testing of Spiked Ground Beef and Ice Cream

To test the functionality of the prototype *Salmonella* assay with real life samples, ground beef and ice cream were purchased from a local supermarket, spiked with a known quantity of *S. Enteritidis* GP60 and grown in buffered peptone water in a Stomacher® sampling bag. At various time points, samples were removed and processed for colony count using XLD agar selective medium and for real-time TMA using the prototype *Salmonella* assay. The various steps followed in this study are described below. A McFarland 1 of *S. Enteritidis* GP60 was made. CFU count confirmation in TSA plates (made dilution to 1E+6 in sterile PBS) was performed. Twenty-five grams of food was weighed and aseptically placed into a Stomacher bag. Twenty CFU were inoculated directly to 225 mL of Buffered Peptone Water. The spiked media was poured into the food-containing Stomacher bag and processed for 2 minutes at 200 rpm, The sample was incubated at 35° C. A 1-mL aliquot was removed (1 aliquot for use in plate count) at times 0, 4, 6, 8, and 24 hours. The sample was plated for CFU counts on selective agar, XLD plates at 3 dilutions, 1 plate/dilution and incubated at 35° C. The remaining five aliquots sampled during a 24-hour period were spun at 12,000×g for 30 seconds. The supernatant was removed and 500 µL of a 50 mM succinate buffer (0.6 M LiCl, 1% LiLS, pH 4.8) was added to the pellet which was then vortexed vigorously for 20 seconds. The sample was heated at >95° C. at least 15 minutes. It was then spun at 12,000×g for 1 minute. The supernatant was transferred to a new labeled tube. Samples were frozen at −70° C. Food controls included: 2 positive and 2 negative for ground beef, 2 positive and 2 negative for plain vanilla ice cream, and 2 positive and 1 negative for the media only pure system.

*Salmonella* CFU Timing and Plate Counts

Using an inoculum of around 12 CFU per 225 ml of media, the spiked *Salmonella* in ground beef grew to around 280 CFU/ml after 4 h of incubation in buffered peptone water (BPW). In spiked ice cream, 20 CFU/ml were observed after 6 h of incubation in BPW. The ground beef was substantially more contaminated than ice cream with other enteric bacteria and had over 1,000 CFU/ml after 4 h of incubation. The spiked media without any food sample had around 20 CFU/ml after 4 h of incubation. By 24 h, all spiked and unspiked food samples in BPW had >1.5E+7 CFU/ml. All negative unspiked media controls did not show any growth. These results corroborate the data obtained from real-time TMA with regards to CFU timing and early emergence of a positive detectable signal using real-time TMA.

For food samples that were spiked with 12 CFU of *Salmonella* per 225 ml BPW, a positive RFU signal for *Salmonella* was observed after 4 h of incubation in either ground beef or ice cream. The unspiked ground beef control run produced positive signals (due to indigenous microbial contamination) after 8 h of incubation and unspiked ice cream control run showed positive signal after 24 h incubation. In both unspiked food samples, the positive signals emerged very late (>40 min). In the unspiked ground beef sample, these false-positive signals may have be caused by cross-reacting organisms (most probably other enteric bacteria) at a very high nucleic acid load (e.g. >6E+8 copies rRNA/reaction in this sample). In the unspiked ice cream sample, the apparent positive signals were derived from indigenous or contaminating organisms that did not grow in the XLD selective medium, but grew in BPW. The positive control (positive spiked media) was positive at 4-h to 24-h points. The negative control (negative unspiked media) remained negative throughout the whole run. These data indicate that real-time TMA can be used to detect a very low level of *Salmonella* contamination with a minimum of 4 h pre-enrichment in BPW and that the whole process did not require complex sample processing steps, except for two brief (<1 minute) centrifugation steps.

Assay Summary

Amplification and detection oligonucleotides targeting two regions of *Salmonella* nucleic acid, a "450 region" corresponding to from about 380 to about 630 nucleotide base positions of *E. coli* 16S rRNA and a "350 region" corresponding to from about 150 to about 425 nucleotide base positions of *E. coli* 23s rRNA, were designed and synthesized for evaluation. Designs in the 16S-450 region did not yield good oligonucleotide candidates for a *Salmonella* genus assay. The oligonucleotides cross-reacted with *Citrobacter* and *Enterobacter*.

Assay specificity and sensitivity were evaluated using lysed bacterial pellets. CFU and rRNA target levels of the bacterial pellets were estimated by plating and by a direct DNA probe assay.

The *Salmonella* assay was 100% sensitive to 22 strains of *Salmonella* including 6 different subspecies and 16 serotypes of *S. enterica* ssp. One exception was the *S. bongori*, which is genotypically more similar to *E. coli* in the target region than other *Salmonella* species. The *Salmonella* assay was 100% specific against 22 non-*Salmonella* organisms at 1 E+5 copies/assay.

Two food matrices, ice cream and ground beef (25 g), were inoculated with *S. Enteritidis* (~20 CFU) and processed through a Stomacher device in broth. Plating and the real-time TMA were monitored over a 24-hour time course. The real-time TMA system utilized two fluorescent probes, one specific for the analyte, one specific for an internal control. The results were analyzed based on fluorescence emergence curves. The real-time TMA assay was run in less than four hours, reducing the time needed for testing in food facilities from days to hours. Results indicated that low level *Salmonella* contamination could be detected within 8 hours, which included 4 hours of pre-enrichment in a non-selective medium followed by sample processing and real-time TMA. In the presence of food, sensitivity was ~8000 copies (~8 CFU/gram food). Interference from high nucleic acid load started at 1.8E+10 copies (~1.8E+7 CFU)/gram food after 8 h growth.

In summary, real-time TMA technology was suitable for rapid, highly sensitive detection of food-borne pathogens. The assay had a sensitivity of 1 E+4 rRNA copies/assay (approximately 10 CFU) for the desired species, *Salmonella enterica* ssp. *enterica* sv. Enteritidis GP60/ATCC13076, while excluding various nearest neighbors and potentially co-contaminating flora at 1E+7 rRNA copies/assay (approximately 10,000 CFU). Utilizing magnetic particle target capture technology, interference from ground beef and ice cream samples was not observed. The data demonstrated a rapid test format that allowed screening of food samples within a single 8-hour work shift for *Salmonella* with an improved enrichment protocol.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

The invention claimed is:

1. A composition for use in a nucleic acid amplification assay to detect *Salmonella* in a sample, comprising a T7 provider oligonucleotide and a primer oligonucleotide that each target a sequence in a region of *Salmonella* nucleic acid,
   wherein said T7 provider oligonucleotide and primer oligonucleotide used in said amplification assay target opposite strands of the *Salmonella* nucleic acid sequence to be amplified; and
   wherein said T7 provider oligonucleotide targets a sequence in a region of *Salmonella* nucleic acid corresponding to bases from about 268-320 of *E. coli* 23S rRNA and/or said primer oligonucleotide targets a sequence in a region of *Salmonella* nucleic acid primer oligonucleotide targets a sequence in a region of *Salmonella* nucleic acid corresponding to bases 338-395 of *E. coli* 23S rRNA.

2. The composition of claim 1, wherein said T7 provider oligonucleotide targets a sequence in a region of *Salmonella* nucleic acid corresponding to bases 268-302 or to bases 279-310 of *E. coli* 23S rRNA, and wherein said primer oligonucleotide targets a sequence in a region of *Salmonella* nucleic acid corresponding to bases 349-374 of *E. coli* 23S rRNA.

3. The composition of claim 1 or claim 2, wherein said T7 provider oligonucleotide and said primer oligonucleotide comprises 15-35 nucleotides that are at least 90% complementary to the targeted *Salmonella* nucleic acid sequence.

4. The composition of claim 1, wherein said T7 provider oligonucleotide is selected from the sequences of SEQ ID NOs: 1, 2, 3, 4, 5, 6, 7, 8, 9, 10, 11, 12, 13, 14, 15, 16, 17, 18, 19, 20, 21, 22, 23, 24, 25, and 26.

5. The composition of claim 1, wherein said primer oligonucleotide is selected from the sequences of SEQ ID NOs: 35, 36, 37, 38, 39, 40, 41, 42, 43, 44, 45, 46, 47, 48, 49, 50, and 51.

6. The composition of claim 1, wherein said T7 provider oligonucleotide is the sequence of SEQ ID NO: 17 or complement thereof, and said primer oligonucleotide is the sequence of SEQ ID NO: 50.

7. The composition of claim 1, wherein said T7 provider oligonucleotide is the sequence of SEQ ID NO: 26 or complement thereof, and said primer oligonucleotide is the sequence of SEQ ID NO: 49.

8. The composition of claim 1 or claim 2, further comprising a blocker oligonucleotide.

9. A kit for use in a *Salmonella* nucleic acid amplification assay comprising the composition according to claim 1.

10. The kit of claim 9, further comprising a detection oligonucleotide.

11. The kit of claim 10, wherein said detection oligonucleotide is a torch oligonucleotide or molecular beacon.

12. A method for detecting *Salmonella* in a sample, said method comprising performing a nucleic acid amplification assay using the T7 provider oligonucleotide and the primer oligonucleotide composition of claim 1.

13. The method of claim 12, wherein detecting said amplified nucleic acid occurs in real-time.

14. The method of claim 12 or claim 13, wherein *Salmonella* nucleic acid is specifically detected in the presence of at least one of: *E. coli, Enterobacter, Citrobacter, Shigella, Pseudomonas* and *Listeria*.

15. The method of claim 12, wherein *Salmonella* nucleic acid is specifically detected in the presence of at least one of: *E. coli, E. vulneris, E. hermannii, E. cloacae, E. aerogenes, E. hoshinae, P. mirabilis, C. brakii, P. fluorescens, S. flexneri, C. freundii, C. koseri/diversus, K. pneumoniae, S. marcescens, L. innocua, E. faecalis, C. jejuni, C. coli*, and *S. pneumoniae*.

* * * * *

```
                        SEQUENCE LISTING

<160> NUMBER OF SEQ ID NOS: 150

<210> SEQ ID NO 1
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 1
aatttaatac gactcactat agggagaatc agcttgtgtg ttagtggaag c            51

<210> SEQ ID NO 2
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 2
aatttaatac gactcactat agggagaagt ggaagcgtct ggaaaggcgc g            51

<210> SEQ ID NO 3
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 3
aatttaatac gactcactat agggagagtt agtggaagcg tctggaaagg c            51

<210> SEQ ID NO 4
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
```

```
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 4
aatttaatac gactcactat agggagatag tggaagcgtc tggaaaggcg c          51

<210> SEQ ID NO 5
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 5
aatttaatac gactcactat agggagagga agcgtctgga aaggcgcgcg a          51

<210> SEQ ID NO 6
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 6
aatttaatac gactcactat agggagacca gagcctgaat cagcttgtgt g          51

<210> SEQ ID NO 7
<211> LENGTH: 54
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (54)..(54)
<223> OTHER INFORMATION: Blocking Moiety

<400> SEQUENCE: 7
aatttaatac gactcactat agggagacgt gtgtgttagt ggaagcgtct ggaa       54

<210> SEQ ID NO 8
<211> LENGTH: 53
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
```

<222> LOCATION: (53)..(53)
<223> OTHER INFORMATION: Blocking Moiety

<400> SEQUENCE: 8
aatttaatac gactcactat agggagacgt gtgtgttagt ggaagcgtct gga        53

<210> SEQ ID NO 9
<211> LENGTH: 52
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (52)..(52)
<223> OTHER INFORMATION: Blocking Moiety

<400> SEQUENCE: 9
aatttaatac gactcactat agggagacgt gtgtgttagt ggaagcgtct gg         52

<210> SEQ ID NO 10
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 10
aatttaatac gactcactat agggagacca caaatcagct tgtgtgttag tggaagc    57

<210> SEQ ID NO 11
<211> LENGTH: 63
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (63)..(63)
<223> OTHER INFORMATION: Blocking Moiety

<400> SEQUENCE: 11
aatttaatac gactcactat agggagacca caacggttta tcagcttgtg tgttagtgga  60
agc                                                               63

<210> SEQ ID NO 12
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety -continued

<400> SEQUENCE: 12
aatttaatac gactcactat agggagaatc agcatgtgtg ttagtggaag c            51

<210> SEQ ID NO 13
<211> LENGTH: 63
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (63)..(63)
<223> OTHER INFORMATION: Blocking Moiety

<400> SEQUENCE: 13
aatttaatac gactcactat agggagacca caacggttta tcagcatgtg tgttagtgga    60
agc                                                                 63

<210> SEQ ID NO 14
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 14
aatttaatac gactcactat agggagaatc agcgtgtgtg ttagtggaag c            51

<210> SEQ ID NO 15
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 15
aatttaatac gactcactat agggagaatc agctggtgtg ttagtggaag c            51

<210> SEQ ID NO 16
<211> LENGTH: 63
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (63)..(63)
<223> OTHER INFORMATION: Blocking Moiety

<400> SEQUENCE: 16

```
aatttaatac gactcactat agggagacca caacggttta tcagctggtg tgttagtgga    60
agc                                                                  63
```

<210> SEQ ID NO 17
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 17

```
aatttaatac gactcactat agggagaatc agcaggtgtg ttagtggaag c             51
```

<210> SEQ ID NO 18
<211> LENGTH: 63
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (63)..(63)
<223> OTHER INFORMATION: Blocking Moiety

<400> SEQUENCE: 18

```
aatttaatac gactcactat agggagacca caacggttta tcagcaggtg tgttagtgga    60
agc                                                                  63
```

<210> SEQ ID NO 19
<211> LENGTH: 52
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (52)..(52)
<223> OTHER INFORMATION: Blocking Moiety

<400> SEQUENCE: 19

```
aatttaatac gactcactat agggagaatc agcttgtgtg ttagtggaag cg            52
```

<210> SEQ ID NO 20
<211> LENGTH: 53
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (53)..(53)
<223> OTHER INFORMATION: Blocking Moiety

<400> SEQUENCE: 20
aatttaatac gactcactat agggagaatc agcttgtgtg ttagtggaag cgt    53

<210> SEQ ID NO 21
<211> LENGTH: 54
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (54)..(54)
<223> OTHER INFORMATION: Blocking Moiety

<400> SEQUENCE: 21
aatttaatac gactcactat agggagaatc agcttgtgtg ttagtggaag cgtc    54

<210> SEQ ID NO 22
<211> LENGTH: 56
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (56)..(56)
<223> OTHER INFORMATION: Blocking Moiety

<400> SEQUENCE: 22
aatttaatac gactcactat agggagaatc agcttgtgtg ttagtggaag cgtctg    56

<210> SEQ ID NO 23
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 23
aatttaatac gactcactat agggagaatc agcttgtgtg ttagtggaag cgtctgg    57

<210> SEQ ID NO 24
<211> LENGTH: 58
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (58)..(58)
<223> OTHER INFORMATION: Blocking Moiety

<400> SEQUENCE: 24
aatttaatac gactcactat agggagaatc agcttgtgtg ttagtggaag cgtctgga    58

```
<210> SEQ ID NO 25
<211> LENGTH: 59
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (59)..(59)
<223> OTHER INFORMATION: Blocking Moiety

<400> SEQUENCE: 25
aatttaatac gactcactat agggagaatc agcttgtgtg ttagtggaag cgtctggaa      59

<210> SEQ ID NO 26
<211> LENGTH: 55
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (55)..(55)
<223> OTHER INFORMATION: Blocking Moiety

<400> SEQUENCE: 26
aatttaatac gactcactat agggagaatc agcttgtgtg ttagtggaag cgtct           55

<210> SEQ ID NO 27
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 27
aatttaatac gactcactat agggagaatc agcacgtgtg ttagtggaag c               51

<210> SEQ ID NO 28
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 28
aatttaatac gactcactat agggagaatc agcatgcgtg ttagtggaag c               51

<210> SEQ ID NO 29
<211> LENGTH: 51
<212> TYPE: DNA
<213> ORGANISM: Artificial
```

```
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 29
aatttaatac gactcactat agggagaatc agcatgtgcg ttagtggaag c          51

<210> SEQ ID NO 30
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 30
aatttaatac gactcactat agggagaatc agcatgtgtg ctagtggaag c          51

<210> SEQ ID NO 31
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 31
aatttaatac gactcactat agggagaatc agcatgtgtg ttagcggaag c          51

<210> SEQ ID NO 32
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 32
aatttaatac gactcactat agggagaatc agcaagtgtg ttagtggaag c          51

<210> SEQ ID NO 33
<211> LENGTH: 61
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
```

```
<222> LOCATION: (1)..(27)
<220> FEATURE:
<221> NAME/KEY: modified_base
<222> LOCATION: (61)..(61)
<223> OTHER INFORMATION: Blocking Moiety

<400> SEQUENCE: 33
aatttaatac gactcactat agggagacca caaatcagct tgtgtgttag tggaagcgtc    60
t                                                                    61

<210> SEQ ID NO 34
<211> LENGTH: 67
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (67)..(67)
<223> OTHER INFORMATION: Blocking Moiety

<400> SEQUENCE: 34
aatttaatac gactcactat agggagacca caacggttta tcagcttgtg tgttagtgga    60
agcgtct                                                              67

<210> SEQ ID NO 35
<211> LENGTH: 15
<212> TYPE: DNA
<213> ORGANISM: Artificial
<220> FEATURE:
<223> OTHER INFORMATION: Amplificiation and Detection Oligonucleotide

<400> SEQUENCE: 35
tcacagcaca tgcgc                                                     15

<210> SEQ ID NO 36
<211> LENGTH: 16
<212> TYPE: DNA
<213> ORGANISM: Artificial
<220> FEATURE:
<223> OTHER INFORMATION: Amplification and Detection Oligonucleotide

<400> SEQUENCE: 36
ctcacagcac atgcgc                                                    16

<210> SEQ ID NO 37
<211> LENGTH: 17
<212> TYPE: DNA
<213> ORGANISM: Artificial
<220> FEATURE:
<223> OTHER INFORMATION: Amplification and Detection Oligonucleotide

<400> SEQUENCE: 37
gctcacagca catgcgc                                                   17

<210> SEQ ID NO 38
<211> LENGTH: 18
<212> TYPE: DNA
<213> ORGANISM: Artificial
<220> FEATURE:
<223> OTHER INFORMATION: Amplification and Detection Oligonucleotide

<400> SEQUENCE: 38
agctcacagc acatgcgc                                                  18
```

<210> SEQ ID NO 39
<211> LENGTH: 18
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (15)..(15)
<223> OTHER INFORMATION: 2'-O-methyl RNA

<400> SEQUENCE: 39
agctcacagc acatccgc                                                   18

<210> SEQ ID NO 40
<211> LENGTH: 20
<212> TYPE: DNA
<213> ORGANISM: Artificial
<220> FEATURE:
<223> OTHER INFORMATION: Amplification and Detection Oligonucleotide

<400> SEQUENCE: 40
cgagctcaca gcacatgcgc                                                 20

<210> SEQ ID NO 41
<211> LENGTH: 20
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 41
cgagctcaca gcacatgcgc                                                 20

<210> SEQ ID NO 42
<211> LENGTH: 20
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 42
cgagctcaca gcacatccgc                                                 20

<210> SEQ ID NO 43
<211> LENGTH: 22
<212> TYPE: DNA
<213> ORGANISM: Artificial
<220> FEATURE:
<223> OTHER INFORMATION: Amplification and Detection Oligonucleotide

<400> SEQUENCE: 43
atcgagctca cagcacatgc gc                                              22

<210> SEQ ID NO 44
<211> LENGTH: 22
<212> TYPE: DNA

```
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 44
aucgagctca cagcacatgc gc                                              22

<210> SEQ ID NO 45
<211> LENGTH: 22
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 45
aucgagctca cagcacatcc gc                                              22

<210> SEQ ID NO 46
<211> LENGTH: 27
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 46
acucatcgag ctcacagcac atgcgct                                         27

<210> SEQ ID NO 47
<211> LENGTH: 20
<212> TYPE: DNA
<213> ORGANISM: Artificial
<220> FEATURE:
<223> OTHER INFORMATION: Amplification and Detection Oligonucleotide

<400> SEQUENCE: 47
cgagctcaca gcacatccgc                                                 20

<210> SEQ ID NO 48
<211> LENGTH: 22
<212> TYPE: DNA
<213> ORGANISM: Artificial
<220> FEATURE:
<223> OTHER INFORMATION: Amplification and Detection Oligonucleotide

<400> SEQUENCE: 48
atcgagctca cagcacatcc gc                                              22

<210> SEQ ID NO 49
<211> LENGTH: 18
<212> TYPE: DNA
<213> ORGANISM: Artificial
<220> FEATURE:
<223> OTHER INFORMATION: Amplification and Detection Oligonucleotide

<400> SEQUENCE: 49
```

```
agctcacagc agatccgc                                              18

<210> SEQ ID NO 50
<211> LENGTH: 18
<212> TYPE: DNA
<213> ORGANISM: Artificial
<220> FEATURE:
<223> OTHER INFORMATION: Amplification and Detection Oligonucleotide

<400> SEQUENCE: 50
agctcacagc acctccgc                                              18

<210> SEQ ID NO 51
<211> LENGTH: 18
<212> TYPE: DNA
<213> ORGANISM: Artificial
<220> FEATURE:
<223> OTHER INFORMATION: Amplification and Detection Oligonucleotide

<400> SEQUENCE: 51
agctcacagc agctccgc                                              18

<210> SEQ ID NO 52
<211> LENGTH: 28
<212> TYPE: DNA
<213> ORGANISM: Artificial
<220> FEATURE:
<223> OTHER INFORMATION: Amplification and Detection Oligonucleotide

<400> SEQUENCE: 52
gctcacagca catgcgcttt tgtgtacg                                   28

<210> SEQ ID NO 53
<211> LENGTH: 32
<212> TYPE: DNA
<213> ORGANISM: Artificial
<220> FEATURE:
<223> OTHER INFORMATION: Amplification and Detection Oligonucleotide

<400> SEQUENCE: 53
ctcatcgagc tcacagcaca tgcgcttttg tg                              32

<210> SEQ ID NO 54
<211> LENGTH: 24
<212> TYPE: DNA
<213> ORGANISM: Artificial
<220> FEATURE:
<223> OTHER INFORMATION: Amplification and Detection Oligonucleotide

<400> SEQUENCE: 54
ccctactcat cgagctcaca gcac                                       24

<210> SEQ ID NO 55
<211> LENGTH: 25
<212> TYPE: DNA
<213> ORGANISM: Artificial
<220> FEATURE:
<223> OTHER INFORMATION: Amplification and Detection Oligonucleotide

<400> SEQUENCE: 55
ggataccacg tgtcccgccc tactc                                      25

<210> SEQ ID NO 56
<211> LENGTH: 31
<212> TYPE: DNA
<213> ORGANISM: Artificial
```

```
<220> FEATURE:
<223> OTHER INFORMATION: Amplification and Detection Oligonucleotide

<400> SEQUENCE: 56
cgagctcaca gcacatgcgc ttttgtgtac g                                   31

<210> SEQ ID NO 57
<211> LENGTH: 18
<212> TYPE: DNA
<213> ORGANISM: Artificial
<220> FEATURE:
<223> OTHER INFORMATION: Amplification and Detection Oligonucleotide

<400> SEQUENCE: 57
agctcacagc acatgccc                                                  18

<210> SEQ ID NO 58
<211> LENGTH: 31
<212> TYPE: DNA
<213> ORGANISM: Artificial
<220> FEATURE:
<223> OTHER INFORMATION: Amplification and Detection Oligonucleotide

<400> SEQUENCE: 58
cgagctcaca gcacacgcgc ttttgtgtac g                                   31

<210> SEQ ID NO 59
<211> LENGTH: 21
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: modified_base
<222> LOCATION: (21)..(21)
<223> OTHER INFORMATION: Blocking Moiety

<400> SEQUENCE: 59
cugauucagg cucugggcuc c                                              21

<210> SEQ ID NO 60
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: modified_base
<222> LOCATION: (20)..(20)
<223> OTHER INFORMATION: Blocking Moiety

<400> SEQUENCE: 60
ccacuaacac acacgcugau                                                20

<210> SEQ ID NO 61
<211> LENGTH: 22
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
```

```
<221> NAME/KEY: modified_base
<222> LOCATION: (22)..(22)
<223> OTHER INFORMATION: Blocking Moiety

<400> SEQUENCE: 61
cuaacacaca cgcugauuca gg                                              22

<210> SEQ ID NO 62
<211> LENGTH: 24
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: modified_base
<222> LOCATION: (24)..(24)
<223> OTHER INFORMATION: Blocking Moiety

<400> SEQUENCE: 62
cacuaacaca cacgcugauu cagg                                            24

<210> SEQ ID NO 63
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 63
cuuccacuaa cacacacgcu                                                 20

<210> SEQ ID NO 64
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 64
ucugggcucc uccccguucg                                                 20

<210> SEQ ID NO 65
<211> LENGTH: 21
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: modified_base
<222> LOCATION: (21)..(21)
<223> OTHER INFORMATION: Blocking Moiety

<400> SEQUENCE: 65
acacgcugau ucaggcucug g                                               21

<210> SEQ ID NO 66
<211> LENGTH: 21
<212> TYPE: RNA
```

```
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (16)..(17)
<223> OTHER INFORMATION: Non-nucleotide spacer

<400> SEQUENCE: 66
ggcugucacc cuguaucagc c                                              21

<210> SEQ ID NO 67
<211> LENGTH: 24
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (5)..(6)
<223> OTHER INFORMATION: Non-nucleotide spacer

<400> SEQUENCE: 67
cgcgcuguca cccuguaucg cgcg                                           24

<210> SEQ ID NO 68
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (15)..(16)
<223> OTHER INFORMATION: Non-nucleotide spacer

<400> SEQUENCE: 68
cacccuguau cgcgcgggug                                                20

<210> SEQ ID NO 69
<211> LENGTH: 27
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (22)..(23)
<223> OTHER INFORMATION: Non-nucleotide spacer

<400> SEQUENCE: 69
cacccuguau cgcgcgccuu ucgggug                                        27

<210> SEQ ID NO 70
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
```

```
<221> NAME/KEY: misc_feature
<223> OTHER INFORMATION: 2'-O-methyl RNA
<220> FEATURE:
<221> NAME/KEY: misc_feature
<222> LOCATION: (4)..(5)
<223> OTHER INFORMATION: Non-nucleotide spacer

<400> SEQUENCE: 70 cccgcuuuu guguacgggg                                          20

<210> SEQ ID NO 71
<211> LENGTH: 52
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(19)
<223> OTHER INFORMATION: 2'-O-Methyl RNA

<400> SEQUENCE: 71
ccgguucgcc ucauuaaccu uuaaaaaaaa aaaaaaaaaa aaaaaaaaaa aa      52

<210> SEQ ID NO 72
<211> LENGTH: 55
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(22)
<223> OTHER INFORMATION: 2'-O-Methyl RNA

<400> SEQUENCE: 72
ccucggggua cuuagauguu ucuuuaaaaa aaaaaaaaaa aaaaaaaaaa aaaaa   55

<210> SEQ ID NO 73
<211> LENGTH: 57
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(24)
<223> OTHER INFORMATION: 2'-O-Methyl RNA

<400> SEQUENCE: 73
ggaaucucgg uugauuucuu uuccuuuaaa aaaaaaaaaa aaaaaaaaaa aaaaaaa 57

<210> SEQ ID NO 74
<211> LENGTH: 53
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(20)
<223> OTHER INFORMATION: 2'-O-Methyl RNA

<400> SEQUENCE: 74
ccguucgcuc gccgcuacug uuuaaaaaaa aaaaaaaaaa aaaaaaaaaa aaa     53

<210> SEQ ID NO 75
<211> LENGTH: 54
<212> TYPE: DNA
<213> ORGANISM: Artificial
```

```
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(21)
<223> OTHER INFORMATION: 2'-O-Methyl RNA

<400> SEQUENCE: 75
cugauucagg cucugggcuc ctttaaaaaa aaaaaaaaaa aaaaaaaaaa aaaa          54

<210> SEQ ID NO 76
<211> LENGTH: 54
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(21)
<223> OTHER INFORMATION: 2'-O-Methyl RNA

<400> SEQUENCE: 76
cagacaggau accacguguc cuuuaaaaaa aaaaaaaaaa aaaaaaaaaa aaaa          54

<210> SEQ ID NO 77
<211> LENGTH: 54
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(21)
<223> OTHER INFORMATION: 2'-O-Methyl RNA

<400> SEQUENCE: 77
cccauauuca gacaggauac cuuuaaaaaa aaaaaaaaaa aaaaaaaaaa aaaa          54

<210> SEQ ID NO 78
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA

<400> SEQUENCE: 78
gcggcauggc ugcauccgga                                                20

<210> SEQ ID NO 79
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA
<220> FEATURE:
<221> NAME/KEY: modified_base
<222> LOCATION: (20)..(20)
<223> OTHER INFORMATION: Blocking Moiety

<400> SEQUENCE: 79
cauacacgcg gcauggcugc                                                20

<210> SEQ ID NO 80
<211> LENGTH: 20
```

```
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA
<220> FEATURE:
<221> NAME/KEY: modified_base
<222> LOCATION: (20)..(20)
<223> OTHER INFORMATION: Blocking Moiety

<400> SEQUENCE: 80
uucauacacg cggcauggcu                                              20

<210> SEQ ID NO 81
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA
<220> FEATURE:
<221> NAME/KEY: modified_base
<222> LOCATION: (20)..(20)
<223> OTHER INFORMATION: Blocking Moiety

<400> SEQUENCE: 81
ccuucuucau acacgcggca                                              20

<210> SEQ ID NO 82
<211> LENGTH: 16
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA
<220> FEATURE:
<221> NAME/KEY: modified_base
<222> LOCATION: (16)..(16)
<223> OTHER INFORMATION: Blocking Moiety

<400> SEQUENCE: 82
cuucuucaua cacgcg                                                  16

<210> SEQ ID NO 83
<211> LENGTH: 18
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA
<220> FEATURE:
<221> NAME/KEY: modified_base
<222> LOCATION: (18)..(18)
<223> OTHER INFORMATION: Blocking Moiety

<400> SEQUENCE: 83
gccuucuuca uacacgcg                                                18

<210> SEQ ID NO 84
<211> LENGTH: 20
<212> TYPE: RNA
<213> ORGANISM: Artificial
<220> FEATURE:
<223> OTHER INFORMATION: Amplification and Detection Oligonucleotide
```

```
<220> FEATURE:
<221> NAME/KEY: misc_feature
<223> OTHER INFORMATION: 2'-O-Methyl RNA
<220> FEATURE:
<221> NAME/KEY: modified_base
<222> LOCATION: (20)..(20)
<223> OTHER INFORMATION: Blocking Moiety

<400> SEQUENCE: 84
aggccuucuu cauacacgcg                                                   20

<210> SEQ ID NO 85
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA

<400> SEQUENCE: 85
gaaggccuuc uucauacacg                                                   20

<210> SEQ ID NO 86
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA
<220> FEATURE:
<221> NAME/KEY: modified_base
<222> LOCATION: (20)..(20)
<223> OTHER INFORMATION: Blocking Moiety

<400> SEQUENCE: 86
gaaggccuuc uucauacacg                                                   20

<210> SEQ ID NO 87
<211> LENGTH: 19
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA
<220> FEATURE:
<221> NAME/KEY: modified_base
<222> LOCATION: (19)..(19)
<223> OTHER INFORMATION: Blocking Moiety

<400> SEQUENCE: 87
caacccgaag gccuucuuc                                                    19

<210> SEQ ID NO 88
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA

<400> SEQUENCE: 88
aguacuuuac aacccgaagg                                                   20
```

```
<210> SEQ ID NO 89
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-Methyl RNA

<400> SEQUENCE: 89
cgcugaaagu acuuacaac                                                  20

<210> SEQ ID NO 90
<211> LENGTH: 50
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (50)..(50)
<223> OTHER INFORMATION: Blocking Moiety

<400> SEQUENCE: 90
atttaatacg actcactata gggagagccg cgtgtatgaa gaaggccttc                 50

<210> SEQ ID NO 91
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 91
aatttaatac gactcactat agggagagtg tatgaagaag gccttcgggt tgtaaag        57

<210> SEQ ID NO 92
<211> LENGTH: 52
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (52)..(52)
<223> OTHER INFORMATION: Blocking Moiety

<400> SEQUENCE: 92
atttaatacg actcactata gggagaatga agaaggcctt cggttgtaa ag              52

<210> SEQ ID NO 93
<211> LENGTH: 47
<212> TYPE: DNA
<213> ORGANISM: Artificial
<220> FEATURE:
<223> OTHER INFORMATION: Amplification and Detection Oligonucleotide
<220> FEATURE:
```

```
<221> NAME/KEY: promoter
<222> LOCATION: (1)..(27)
<220> FEATURE:
<221> NAME/KEY: modified_base
<222> LOCATION: (47)..(47)
<223> OTHER INFORMATION: Blocking Moiety

<400> SEQUENCE: 93
atttaatacg actcactata gggagagaag gccttcgggt tgtaaag                47

<210> SEQ ID NO 94
<211> LENGTH: 53
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (53)..(53)
<223> OTHER INFORMATION: Blocking Moiety

<400> SEQUENCE: 94
atttaatacg actcactata gggagaccac aagaaggcct tcggttgta aag          53

<210> SEQ ID NO 95
<211> LENGTH: 49
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (49)..(49)
<223> OTHER INFORMATION: Blocking Moiety

<400> SEQUENCE: 95
atttaatacg actcactata gggagagaag gccttcgggt tgtaaagta              49

<210> SEQ ID NO 96
<211> LENGTH: 52
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (52)..(52)
<223> OTHER INFORMATION: Blocking Moiety

<400> SEQUENCE: 96
atttaatacg actcactata gggagagaag gccttcgggt tgtaaagtac tt          52

<210> SEQ ID NO 97
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
```

<222> LOCATION: (57)..(57)
<223> OTHER INFORMATION: Blocking Moiety

<400> SEQUENCE: 97
aatttaatac gactcactat agggagaggc cttcgggttg taaagtactt tcagcgg      57

<210> SEQ ID NO 98
<211> LENGTH: 49
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (49)..(49)
<223> OTHER INFORMATION: Blocking Moiety

<400> SEQUENCE: 98
atttaatacg actcactata gggagacctt cgggttgtaa agtactttc                49

<210> SEQ ID NO 99
<211> LENGTH: 49
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (49)..(49)
<223> OTHER INFORMATION: Blocking Moiety

<400> SEQUENCE: 99
atttaatacg actcactata gggagagggt tgtaaagtac tttcagcgg                49

<210> SEQ ID NO 100
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 100
aatttaatac gactcactat agggagagtt gtaaagtact ttcagcgggg aggaagg      57

<210> SEQ ID NO 101
<211> LENGTH: 48
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (48)..(48)
<223> OTHER INFORMATION: Blocking Moiety

<400> SEQUENCE: 101
atttaatacg actcactata gggagagtac tttcagcggg gaggaagg         48

<210> SEQ ID NO 102
<211> LENGTH: 48
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (48)..(48)
<223> OTHER INFORMATION: Blocking Moiety

<400> SEQUENCE: 102
atttaatacg actcactata gggagagtac tttcagcggg gaggaagg         48

<210> SEQ ID NO 103
<211> LENGTH: 56
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (56)..(56)
<223> OTHER INFORMATION: Blocking Moiety

<400> SEQUENCE: 103
atttaatacg actcactata gggagagtac tttcagcggg gaggaaggga gtaaag    56

<210> SEQ ID NO 104
<211> LENGTH: 49
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (49)..(49)
<223> OTHER INFORMATION: Blocking Moiety

<400> SEQUENCE: 104
atttaatacg actcactata gggagacagc ggggaggaag ggagtaaag        49

<210> SEQ ID NO 105
<211> LENGTH: 21
<212> TYPE: DNA
<213> ORGANISM: Artificial
<220> FEATURE:
<223> OTHER INFORMATION: Amplification and Detection Oligonucleotide

<400> SEQUENCE: 105
tactttcagc ggggaggaag g                                      21

<210> SEQ ID NO 106
<211> LENGTH: 24
<212> TYPE: DNA
<213> ORGANISM: Artificial
<220> FEATURE:
<223> OTHER INFORMATION: Amplification and Detection Oligonucleotide

```
<400> SEQUENCE: 106
tactttcagc ggggaggaag ggag                                             24

<210> SEQ ID NO 107
<211> LENGTH: 24
<212> TYPE: DNA
<213> ORGANISM: Artificial
<220> FEATURE:
<223> OTHER INFORMATION: Amplification and Detection Oligonucleotide

<400> SEQUENCE: 107
cgggttgtaa agtactttca gcgg                                             24

<210> SEQ ID NO 108
<211> LENGTH: 44
<212> TYPE: DNA
<213> ORGANISM: Artificial
<220> FEATURE:
<223> OTHER INFORMATION: Amplification and Detection Oligonucleotide

<400> SEQUENCE: 108
gaacctagtt gggcgagtta cggagtaacg tcaattgctg cggt                       44

<210> SEQ ID NO 109
<211> LENGTH: 20
<212> TYPE: DNA
<213> ORGANISM: Artificial
<220> FEATURE:
<223> OTHER INFORMATION: Amplification and Detection Oligonucleotide

<400> SEQUENCE: 109
gtaacgtcaa ttgctgcggt                                                  20

<210> SEQ ID NO 110
<211> LENGTH: 20
<212> TYPE: DNA
<213> ORGANISM: Artificial
<220> FEATURE:
<223> OTHER INFORMATION: Amplification and Detection Oligonucleotide

<400> SEQUENCE: 110
ggtaacgtca attgctgcgg                                                  20

<210> SEQ ID NO 111
<211> LENGTH: 44
<212> TYPE: DNA
<213> ORGANISM: Artificial
<220> FEATURE:
<223> OTHER INFORMATION: Amplification and Detection Oligonucleotide

<400> SEQUENCE: 111
gaacctagtt gggcgagtta cggaggtaac gtcaattgct gcgg                       44

<210> SEQ ID NO 112
<211> LENGTH: 22
<212> TYPE: DNA
<213> ORGANISM: Artificial
<220> FEATURE:
<223> OTHER INFORMATION: Amplification and Detection Oligonucleotide

<400> SEQUENCE: 112
ctgcgggtaa cgtcaattgc tg                                               22

<210> SEQ ID NO 113
<211> LENGTH: 46
<212> TYPE: DNA
```

```
<213> ORGANISM: Artificial
<220> FEATURE:
<223> OTHER INFORMATION: Amplification and Detection Oligonucleotide

<400> SEQUENCE: 113
gaacctagtt gggcgagtta cggactgcgg gtaacgtcaa ttgctg                    46

<210> SEQ ID NO 114
<211> LENGTH: 53
<212> TYPE: DNA
<213> ORGANISM: Artificial
<220> FEATURE:
<223> OTHER INFORMATION: Amplification and Detection Oligonucleotide

<400> SEQUENCE: 114
gtttgtatgt ctgttgctat tatgtctacc ttcttctgcg ggtaacgtca atg            53

<210> SEQ ID NO 115
<211> LENGTH: 21
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 115
cacggagtta gccggugctt c                                               21

<210> SEQ ID NO 116
<211> LENGTH: 28
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 116
cugctggcac ggagttagcc ggtgcttc                                        28

<210> SEQ ID NO 117
<211> LENGTH: 57
<212> TYPE: DNA
<213> ORGANISM: Artificial
<220> FEATURE:
<223> OTHER INFORMATION: Amplification and Detection Oligonucleotide

<400> SEQUENCE: 117
gtttgtatgt ctgttgctat tatgtctacc tgctggcacg gagttagccg gtgcttc        57

<210> SEQ ID NO 118
<211> LENGTH: 38
<212> TYPE: DNA
<213> ORGANISM: Artificial
<220> FEATURE:
<223> OTHER INFORMATION: Amplification and Detection Oligonucleotide

<400> SEQUENCE: 118
gtctacgcgg ctgctggcac ggagttagcc ggtgcttc                             38

<210> SEQ ID NO 119
```

```
<211> LENGTH: 62
<212> TYPE: DNA
<213> ORGANISM: Artificial
<220> FEATURE:
<223> OTHER INFORMATION: Amplification and Detection Oligonucleotide

<400> SEQUENCE: 119
gaacctagtt gggcgagtta cggagtctac gcggctgctg gcacggagtt agccggtgct      60
tc                                                                     62

<210> SEQ ID NO 120
<211> LENGTH: 19
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 120
cugctggcac ggagttagc                                                   19

<210> SEQ ID NO 121
<211> LENGTH: 27
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 121
cgcutgcacc ctccgtatta ccgcggc                                          27

<210> SEQ ID NO 122
<211> LENGTH: 22
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl RNA

<400> SEQUENCE: 122
cgcutgcacc ctccgtatta cc                                               22

<210> SEQ ID NO 123
<211> LENGTH: 54
<212> TYPE: DNA
<213> ORGANISM: Artificial
<220> FEATURE:
<223> OTHER INFORMATION: Amplification and Detection DNA-RNA Hybrid
      Oligonucleotide

<400> SEQUENCE: 123
gtttgtatgt ctgttgctat tatgtctacg gauttcacat ctgacttaac aaac            54

<210> SEQ ID NO 124
<211> LENGTH: 23
<212> TYPE: RNA
```

```
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 124
ggggcuuuac ucccuuccuc ccc                                              23

<210> SEQ ID NO 125
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (5)..(6)
<223> OTHER INFORMATION: Non-nucleotide spacer

<400> SEQUENCE: 125
ggaggaccac aacaccuucc ucc                                              23

<210> SEQ ID NO 126
<211> LENGTH: 29
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (5)..(6)
<223> OTHER INFORMATION: Non-nucleotide spacer

<400> SEQUENCE: 126
ggagguuauu aaccacaaca ccuuccucc                                        29

<210> SEQ ID NO 127
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (5)..(6)
<223> OTHER INFORMATION: Non-nucleotide spacer

<400> SEQUENCE: 127
cgaggaccac aacaccuucc ucg                                              23

<210> SEQ ID NO 128
<211> LENGTH: 25
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 128
```

```
ccaacuuuac ucccuuccuc guugg                                              25

<210> SEQ ID NO 129
<211> LENGTH: 32
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 129
gcaaagguau uaacuuuacu cccuuccuuu gc                                      32

<210> SEQ ID NO 130
<211> LENGTH: 27
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (6)..(7)
<223> OTHER INFORMATION: Non-nucleotide spacer

<400> SEQUENCE: 130
ggaagguuau uaaccacaac accuucc                                            27

<210> SEQ ID NO 131
<211> LENGTH: 28
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 131
gcaaagguau uaacuuuacu cccuuugc                                           28

<210> SEQ ID NO 132
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 132
gggaggguau uaacuuuacu ccc                                                23

<210> SEQ ID NO 133
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (5)..(6)
```

<223> OTHER INFORMATION: Non-nucleotide spacer

<400> SEQUENCE: 133 cguguuauu aaccacaaca ccg                                             23

<210> SEQ ID NO 134
<211> LENGTH: 21
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (6)..(7)
<223> OTHER INFORMATION: Non-nucleotide spacer

<400> SEQUENCE: 134
gguguuauua accacaacac c                                              21

<210> SEQ ID NO 135
<211> LENGTH: 30
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (5)..(6)
<223> OTHER INFORMATION: Non-nucleotide spacer

<400> SEQUENCE: 135
cgguggcugc gguuauuaac cacaacaccg                                     30

<210> SEQ ID NO 136
<211> LENGTH: 26
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (21)..(22)
<223> OTHER INFORMATION: Non-nucleotide spacer

<400> SEQUENCE: 136
cgcugcgguu auuaaccaca acagcg                                         26

<210> SEQ ID NO 137
<211> LENGTH: 27
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (22)..(23)
<223> OTHER INFORMATION: Non-nucleotide spacer

<400> SEQUENCE: 137

-continued gcugcgguua uuaaccacaa cagcagc                                                27

<210> SEQ ID NO 138
<211> LENGTH: 30
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA
<220> FEATURE:
<221> NAME/KEY: misc_feature
<222> LOCATION: (25)..(26)
<223> OTHER INFORMATION: Non-nucleotide spacer

<400> SEQUENCE: 138
ccugcugcgg uuauuaacca caacagcagg                                             30

<210> SEQ ID NO 139
<211> LENGTH: 30
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 139
ccgaggagca aagguauuaa cuuuacucgg                                             30

<210> SEQ ID NO 140
<211> LENGTH: 29
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 140
cgagcaaagg uauuaacuuu acucgcucg                                              29

<210> SEQ ID NO 141
<211> LENGTH: 28
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 141
cgagcaaagg uauuaacuuu acugcucg                                               28

<210> SEQ ID NO 142
<211> LENGTH: 27
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 142
cgagcaaagg uauuaacuuu acgcucg                                                27

-continued

<210> SEQ ID NO 143
<211> LENGTH: 26
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 143
cgagcaaagg uauuaacuuu agcucg                                          26

<210> SEQ ID NO 144
<211> LENGTH: 25
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 144
cgagcaaagg uauuaacuuu gcucg                                           25

<210> SEQ ID NO 145
<211> LENGTH: 22
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 145
cgagcaaagg uauuaacgcu cg                                              22

<210> SEQ ID NO 146
<211> LENGTH: 21
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 146
ccgucaauga gcaaaggacg g                                               21

<210> SEQ ID NO 147
<211> LENGTH: 28
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 147
cggguaacgu caaugagcaa aggacccg                                        28

<210> SEQ ID NO 148
<211> LENGTH: 29
<212> TYPE: RNA

```
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 148
cugcggguaa cgucaaugag caaacgcag                                      29

<210> SEQ ID NO 149
<211> LENGTH: 25
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl RNA

<400> SEQUENCE: 149
ccugcgggua acgucaauga gcagg                                          25

<210> SEQ ID NO 150
<211> LENGTH: 266
<212> TYPE: DNA
<213> ORGANISM: Artificial
<220> FEATURE:
<223> OTHER INFORMATION: Salmonella enterica sbsp enterica sv
      Enteritidis (ATCC13076) sequence corresponding to 150-425 of E.
      coli 23s rRNA sequence

<400> SEQUENCE: 150
tcacactatc attaactgaa tccataggtt aatgaggcga accgggggaa ctgaaacatc    60
taagtacccc gaggaaaaga aatcaaccga gattccccca gtagcggcga gcgaacgggg   120
aggagcccag agcctgaatc agcatgtgtg ttagtggaag cgtctggaaa ggcgcgcgat   180
acagggtgac agccccgtac acaaaagcgc atgtgctgtg agctcgatga gtagggcggg   240
acacgtggta tcctgtctga atatgg                                        266
```